US009560812B2

(12) United States Patent
Orsley

(10) Patent No.: US 9,560,812 B2
(45) Date of Patent: Feb. 7, 2017

(54) SOLAR REDSHIFT SYSTEMS

(75) Inventor: Timothy James Orsley, San Jose, CA (US)

(73) Assignee: Corning Incorporated, Corning, NY (US)

( * ) Notice: Subject to any disclaimer, the term of this patent is extended or adjusted under 35 U.S.C. 154(b) by 180 days.

(21) Appl. No.: 14/232,467

(22) PCT Filed: Jun. 20, 2012

(86) PCT No.: PCT/US2012/043290
§ 371 (c)(1),
(2), (4) Date: Jan. 13, 2014

(87) PCT Pub. No.: WO2013/019330
PCT Pub. Date: Feb. 7, 2013

(65) Prior Publication Data
US 2014/0137941 A1 May 22, 2014

Related U.S. Application Data

(60) Provisional application No. 61/513,256, filed on Jul. 29, 2011.

(51) Int. Cl.
G02B 6/32 (2006.01)
A01G 9/02 (2006.01)
(Continued)

(52) U.S. Cl.
CPC ............... *A01G 9/02* (2013.01); *A01G 33/00* (2013.01); *C12M 21/02* (2013.01); *C12M 23/50* (2013.01);
(Continued)

(58) Field of Classification Search
CPC ....... A01G 9/02; A01G 33/00; H01L 31/0543; H01L 31/0547; H01L 31/035218; H01L 31/055; C12M 21/02; C12M 23/50; C12M 31/04; C12M 31/06; G02B 5/208; G02B 27/1006; B82Y 20/00; Y02P 60/12; Y02E 10/52; Y10S 977/774
(Continued)

(56) References Cited

U.S. PATENT DOCUMENTS 4,144,097 A 3/1979 Chambers et al.
4,188,238 A 2/1980 Boling ............................ 136/89
(Continued)

FOREIGN PATENT DOCUMENTS

DE 2501907 A1 7/1976
DE 102009046794 A1 5/2011
(Continued)

OTHER PUBLICATIONS

International Searching Authority; International Search Report; Mailing Date: Sep. 13, 2012; pp. 1-2.
(Continued)

*Primary Examiner* — Ryan Lepisto
*Assistant Examiner* — Guy Anderson

(57) ABSTRACT

Solar-redshift systems comprise an integral array of redshift modules, each having at least a focusing device, a target, and a quantum-dot vessel. The quantum-dot vessel contains quantum dots that emit light having an emission wavelength. The focusing device directs incident solar radiation through a focusing gap and toward the quantum-dot vessel, or into a slab waveguide and then toward the quantum-dot vessel, causing the quantum dots to emit redshifted light having the emission wavelength. The redshifted light is directed to the target, examples of which include a photovoltaic material or a living photosynthetic organism. The target has increased sensitivity or response to photons having the wavelength of the redshifted light. A trapping reflector component of the quantum-dot vessel prevents loss of redshifted light to the
(Continued)

environment outside the solar-redshift system and allows undesirable infrared light to be removed from the system.

19 Claims, 11 Drawing Sheets

(51) Int. Cl.
| | |
|---|---|
| A01G 33/00 | (2006.01) |
| G02B 5/20 | (2006.01) |
| G02B 27/10 | (2006.01) |
| H01L 31/055 | (2014.01) |
| H01L 31/0352 | (2006.01) |
| H01L 31/054 | (2014.01) |
| C12M 1/00 | (2006.01) |
| B82Y 20/00 | (2011.01) |

(52) U.S. Cl.
CPC ............ *C12M 31/04* (2013.01); *C12M 31/06* (2013.01); *G02B 5/208* (2013.01); *G02B 27/1006* (2013.01); *H01L 31/035218* (2013.01); *H01L 31/055* (2013.01); *H01L 31/0543* (2014.12); *H01L 31/0547* (2014.12); *B82Y 20/00* (2013.01); *Y02E 10/52* (2013.01); *Y02P 60/12* (2015.11); *Y10S 977/774* (2013.01)

(58) Field of Classification Search
USPC .......................................................... 385/33
See application file for complete search history.

(56) References Cited

U.S. PATENT DOCUMENTS

| | | | |
|---|---|---|---|
| 4,190,465 A | 2/1980 | Boling | |
| 4,264,124 A | 4/1981 | Greubel et al. | |
| 4,425,907 A | 1/1984 | Younghouse | |
| 4,427,838 A | 1/1984 | Goldman | |
| 5,707,458 A | 1/1998 | Nagashima et al. | .......... 136/246 |
| 5,816,238 A | 10/1998 | Burns et al. | |
| 6,476,312 B1* | 11/2002 | Barnham | ............... B82Y 10/00 136/246 |
| 6,538,191 B1 | 3/2003 | MacDonald | |
| 6,689,949 B2 | 2/2004 | Ortabasi | |
| 6,878,871 B2 | 4/2005 | Scher et al. | |
| 6,961,499 B2* | 11/2005 | Lee | ........................ B82Y 10/00 257/E21.09 |
| 7,171,069 B1 | 1/2007 | Laughlin | ........................ 385/18 |
| 7,402,832 B2* | 7/2008 | Lee | ........................ B82Y 10/00 257/17 |
| 7,541,537 B2 | 6/2009 | Madigan | |
| 7,791,157 B2 | 9/2010 | Cho et al. | |
| 8,111,970 B2* | 2/2012 | Herrmann, Jr. | ....... H01L 31/055 136/243 |
| 8,224,132 B2* | 7/2012 | Hermann, Jr. | ...... H01L 31/0549 136/243 |
| 2007/0157967 A1 | 7/2007 | Mershin et al. | .............. 136/263 |
| 2008/0155890 A1 | 7/2008 | Oyler | ............... 47/1.4 |
| 2008/0216894 A1 | 9/2008 | Hammond | .................... 136/263 |
| 2009/0014053 A1 | 1/2009 | Schulz | |
| 2009/0296368 A1 | 12/2009 | Ramer | |
| 2010/0132955 A1 | 6/2010 | Storm, Jr. et al. | |
| 2010/0193011 A1* | 8/2010 | Mapel | ..................... C03C 3/102 136/246 |
| 2010/0218807 A1 | 9/2010 | Arbore et al. | ................ 136/246 |
| 2010/0224248 A1* | 9/2010 | Kenney | ................. H01L 31/055 136/259 |
| 2010/0288344 A1 | 11/2010 | Spitzer | |
| 2010/0323387 A1 | 12/2010 | Bailey et al. | .................... 435/29 |
| 2011/0075251 A1* | 3/2011 | Herrmann, Jr. | ....... H01L 31/055 359/326 |
| 2011/0075961 A1* | 3/2011 | Herrmann, Jr. | ....... H01L 31/055 385/2 |
| 2011/0114174 A1 | 5/2011 | Rennig et al. | |
| 2011/0253198 A1* | 10/2011 | Patrick | ................... B82Y 20/00 136/247 |
| 2014/0315291 A1* | 10/2014 | Higgs | ................... C12M 21/02 435/292.1 |

FOREIGN PATENT DOCUMENTS

| | | | |
|---|---|---|---|
| GB | 2476300 | 6/2011 | .......... H01L 31/052 |
| JP | 2004119879 A | 4/2004 | |
| WO | 2010023657 A2 | 3/2010 | |
| WO | 2010042196 A1 | 4/2010 | |
| WO | 2010042197 A1 | 4/2010 | |
| WO | 2010062713 A3 | 6/2010 | |
| WO | 2010132955 A1 | 11/2010 | |
| WO | 2011011691 A2 | 1/2011 | |
| WO | 2013019330 A1 | 2/2013 | |

OTHER PUBLICATIONS

Dr. Mae-Wan Ho; "Quantum Dots and Ultra-Efficient Solar Cells?"; ISIS Report; Jan. 19, 2006; pp. 1-5.
Kamat; "Workshop on Nanoscience for Solar Energy Conversion"; Oct. 27-29, 2008; pp. 1-49.
Loper et al.; "Silicon Quantum Dot Superstructures for all-silicon tandem solar cells"; Quantsol 2009; pp. 1-4.
The State Intellectual Property Office of the People's Republic of China; Notice on the First Office Action for CN Application No. 201280038258.X; Date of Dispatch: Dec. 16, 2015; pp. 1-5.
European Patent Office; Extended European Search Report for EP Application No. 15187672.9; Jan. 19, 2016; pp. 1-8.
European Patent Office; Extended European Search Report for EP Application No. 12820061,5; Date of Search: Feb. 25, 2015; pp. 1-7.
Japanese Patent Office; Notice First Office Action for JP Application No. 2014-523930; Issue Date: Apr. 5, 2016; pp. 1-4.
Lee et al.; Abstract of "Photoacclimation of Chlorella vulgaris to Red Light from Light-Emitting Diodes Leads to Autospore Release Following Each Cellular Division"; Biotechnology Press, vol. 12, Issue 2 (1996), http://onlinelibrary.wiley.com/doi/10.1021/bp950084t/full; Date Accessed: Sep. 7, 2016.

* cited by examiner

SOLAR REDSHIFT SYSTEMS

CROSS REFERENCE TO RELATED APPLICATIONS

This application claims the benefit of priority under 35 U.S.C. §119(e) to U.S. Provisional Application Ser. No. 61/513,256, filed Jul. 29, 2011.

TECHNICAL FIELD

The present specification relates generally to systems for utilizing solar radiation in energy collecting applications and, more particularly, to systems that convert incident solar radiation to wavelengths that promote energy collection by photovoltaics or photosynthetic organisms.

BACKGROUND

Sunlight can be harnessed as a source of clean energy in a variety of ways. With photovoltaic cells, sunlight strikes a photovoltaic material, exciting electrons in the photovoltaic material and resulting in a potential difference between electrodes placed on the photovoltaic material. This potential difference may be used to power an electric circuit or to store electrical energy in a storage device such as a battery. With living organisms, sunlight causes photosynthesis in an organism such as algae, causing the organism to grow. The organism then may be burned, for example as a carbon-neutral fuel source, and either the organism itself, or the secretions it produces metabolically, may be used as sources of bio-derived molecules, including ethanol and numerous other compounds that otherwise would be derived from petroleum.

SUMMARY

Systems are disclosed herein that optimally utilize solar radiation for producing energy from targets such as photovoltaic materials and/or living photosynthetic organisms. In various embodiments, the systems are solar-redshift systems. In embodiments of solar-redshift systems described herein, quantum dot plates are used to convert high-energy wavelengths in broad-spectrum incident solar radiation to selected lower-energy wavelengths such as for a specific energy-harnessing application. The solar-redshift systems are configured not only to optimize the wavelength spectrum of the solar radiation, but also to maximize the efficiency at which the solar radiation is made available to the energy-harnessing application.

In some embodiments, solar-redshift modules are provided. The solar-redshift modules may include at least one collecting target having a target wavelength, at least one quantum-dot vessel, and a focusing device that focuses incident solar radiation into the solar redshift system. The at least one collecting target may be selected from a growth vessel or a photovoltaic plate. The growth vessel may contain a living photosynthetic organism in a growth medium for sustaining the living photosynthetic organism, such that the target wavelength is a wavelength of increased photosynthetic response of the living photosynthetic organism. The photovolatic plate may include a photovoltaic material, such that the target wavelength is a wavelength of increased sensitivity of the photovoltaic material. The at least one quantum-dot vessel may include a sealed cavity defined between a first plate and a second plate. The first plate of the at least one quantum-dot vessel may be between the second plate and the collecting target. A quantum-dot suspension may be disposed in the sealed cavity and may contain quantum dots that emit redshifted light having the target wavelength when irradiated by incident solar radiation. The quantum-dot vessel may also include a trapping reflector that reflects at least a portion of the redshifted light emitted by the quantum dots toward the collecting target. The focusing device, the at least one quantum-dot vessel, and the at least one collecting target may be configured such that the incident solar radiation focused into the solar redshift system strikes the at least one quantum-dot vessel before striking the at least one collecting target.

In some embodiments, solar-redshift systems are provided. The solar-redshift systems may include an integral array of the solar-redshift modules.

In some embodiments, the solar-redshift systems may be configured as photovoltaic solar-redshift systems or as photosynthesis-enhancing solar-redshift systems. The photovoltaic solar redshift systems may include an integral array of photovoltaic plates that include a photovoltaic material having a wavelength of increased sensitivity. The photosynthesis-enhancing solar-redshift systems may include a growth vessel containing a living photosynthetic organism in a growth medium for sustaining the living photosynthetic organism. The living photosynthetic organism may have a wavelength of increased photosynthetic response In some embodiments, parallel-plate solar-redshift systems are provided. The parallel-plate solar-redshift systems may include a parallel-plate configuration of solar-redshift modules and at least one focusing device. Each solar-redshift module may include at least one solar-radiation conversion assembly and a collecting target. The collecting target may be a growth vessel or a photovoltaic plate, for example. Such a growth vessel may contain a living photosynthetic organism in a growth medium for sustaining the living photosynthetic organism, and the living photosynthetic organism may have a wavelength of increased photosynthetic response. Such a photovoltaic plate may include a photovoltaic material having a wavelength of increased sensitivity. The at least one solar-radiation conversion assembly may include a waveguide, an infrared-radiation absorber, and a quantum dot vessel interposed between the waveguide and the infrared-radiation absorber. The quantum dot vessel contains a quantum-dot suspension of quantum dots that emit redshifted light having the wavelength of increased photosynthetic response or the wavelength of increased sensitivity when irradiated by incident solar radiation. The quantum-dot vessel also may include a trapping reflector that reflects the redshifted light toward the collecting target and transmits infrared light from the incident solar radiation in a direction away from the collecting target. The waveguide of the at least one solar-radiation conversion assembly may be interposed between the quantum dot vessel of the at least one solar-radiation conversion assembly and the collecting target. The waveguide may include a frustrating surface that scatters focused solar radiation within the waveguide toward the quantum dot vessel and permits redshifted light to pass through the waveguide from the quantum dot vessel toward the collecting target. The focusing device focuses incident solar radiation onto sun-facing edges of the waveguides of the solar-radiation conversion assemblies in respective solar-redshift modules.

Additional features and advantages of the embodiments described herein will be set forth in the detailed description that follows. These additional features and advantages should be in part readily apparent to those skilled in the art from the written description alone or should be readily recognized by practicing the embodiments described in the written description that follows, including the appended drawings and claims.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1A:
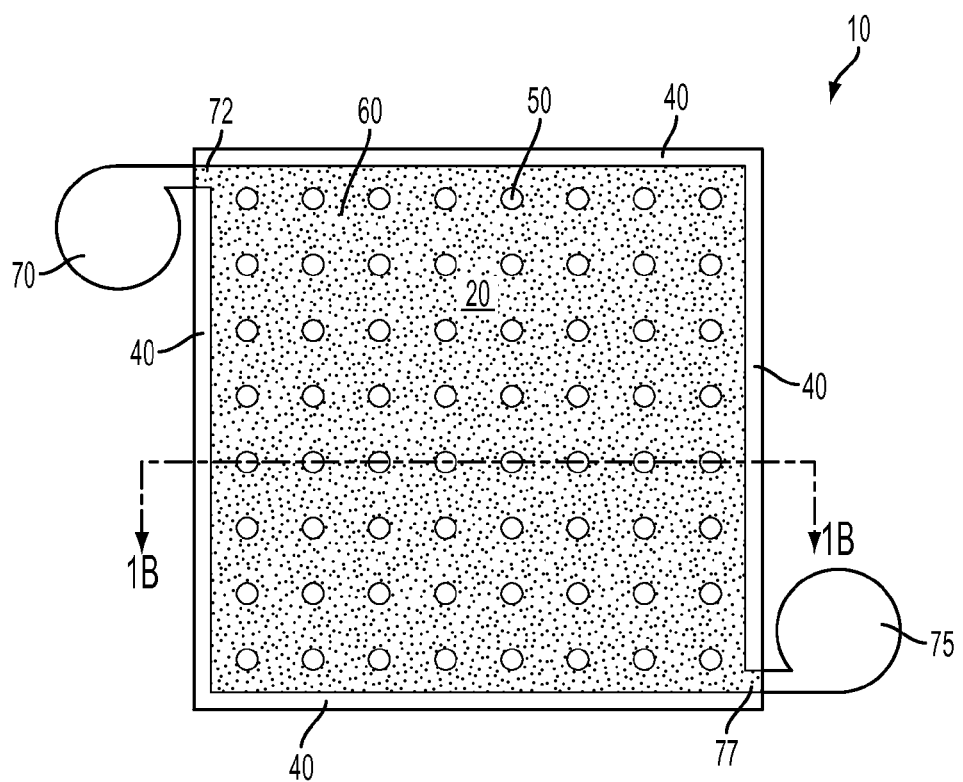
FIG. 1A is a top plan view of a quantum-dot vessel, a component of the solar-redshift systems described herein.

Solar-redshift modules and solar-redshift systems including the solar-redshift modules in various configurations now will be described. The following description initially will detail features common to each of the various embodiments of solar-redshift modules, solar-redshift systems, and configurations thereof. After the initial general description of common features, illustrative embodiments of solar-redshift modules and solar-redshift systems containing the common features will be described with specific references to the appended drawings.

Solar-redshift systems according to various embodiments described herein utilize quantum dots to transform solar radiation to redshifted light with increased proportions of wavelengths useful to a particular energy-harnessing process. In some embodiments described herein, the solar-redshift systems are configured as photovoltaic solar-redshift systems containing photovoltaic solar-redshift modules, and in other embodiments described herein, the solar-redshift systems are configured as photosynthesis-enhancing solar-redshift systems containing photosynthesis-enhancing solar-redshift modules. In further embodiments, hybrid systems may contain both photosynthesis-enhancing elements and photovoltaic elements. In general, these solar-redshift systems have in common both the incorporation of quantum dots to produce redshifted light and also the conservation of the redshifted light through various optical configurations of the systems.

As used herein, the term "solar radiation" refers to electromagnetic radiation produced by the sun, and particularly refers to the electromagnetic radiation with wavelengths ranging from about 100 nm (ultraviolet) to about 1 mm (far-infrared), which includes the entire visible portion of the electromagnetic spectrum (from about 380 nm to about 750 nm). As used herein, the term "incident solar radiation" refers to solar radiation that has passed through the atmosphere and a portion of the solar-redshift systems described herein without any intentional manipulation of the wavelengths of light inherently present in the solar radiation. Typically, all solar radiation entering a solar-redshift system described herein will meet the definition of "incident solar radiation" at least at the instant the solar radiation first enters the solar-redshift system.

The quantum dots in the solar-redshift systems according to various embodiments may be chosen to naturally emit an emission wavelength of light when exposed to light having a wavelength shorter than the emission wavelength. For example, a quantum dot may be chosen to strongly emit red light when exposed to a polychromatic light source containing a high amount of blue light. The emitted light of the emission wavelength then is directed to a collecting target, such as a photovoltaic plate or a living photosynthetic organism, which inherently has increased sensitivity or response to photons having the emission wavelength of the quantum dot over that attained from photons of the shorter wavelengths present in the light before the light encountered the quantum dots.

In each of the solar-redshift systems described herein, the quantum dots are retained in a quantum-dot vessel. The quantum-dot vessel may comprise, for example, two hermetically sealed plates, which may be made of a suitable material such as, for example, glass plates of a desired thickness. As is well understood, quantum dots have an emission wavelength unique to the material of the quantum dots and the size of the quantum dots, wherein photons having a higher energy (shorter wavelength) than the emission wavelength may be absorbed by the quantum dot and subsequently re-emitted as a photon of the emission wavelength. The quantum dots do not absorb photons having a lower energy (longer wavelength) than the emission wavelength of the quantum dots.

When incident solar radiation such as sunlight, for example, passes through the quantum dots sealed between the two plates, photons having a shorter wavelength than the emission wavelength of the quantum dots effectively are shifted to the lower-energy emission wavelength of the quantum dots. Thus, these photons emitted from the quantum dots as referred to hereinafter as "redshifted light."

The unique wavelength of the redshifted light, determined by the material and size of the quantum dots, becomes particularly advantageous in solar-collection systems when the unique wavelength is one desirable for a selected energy-harnessing application. For example, if a living organism such as algae is grown to produce biomass, photosynthesis of the algae may be most active at a certain wavelength unique to the species of algae. For example, photosynthesis in some species of algae is most active at about 680 nm, an emission wavelength easily attainable through selection of appropriate quantum dot materials and sizes. In such an application, redshifted light derived from the full spectrum of incident solar radiation causes wavelengths (green, blue, ultraviolet, for example) that otherwise would have been underutilized to be converted into a more highly useful form of energy, namely, the red light of 680 nm wavelength. Thus, the redshifted light may contribute more efficiently to the growth of the algae than the broad-spectrum incident solar radiation alone would have.

Sunlight includes a very broad spectrum of wavelengths that includes infrared, ultraviolet, and all parts of the visible spectrum. In applications involving photovoltaic cells and biomass production, typically a much narrower spectral range of incident light can be useful toward effective harnessing of the sunlight. For example, cadmium telluride (CdTe) photovoltaic materials respond most efficiently to light having a wavelength of approximately 600 nm (yellow-orange light). Other wavelengths may cause the electrons in the CdTe material to excite, but only at a lower effective sensitivity. As another example, certain varieties of green algae, which appear green because they reflect green light, respond photosynthetically most favorably to light having a wavelength of approximately 680 nm (red light). The reflection of the green light by the green algae is tantamount to wasting the energy that could have been harnessed from the sunlight used to grow the algae. Moreover, wavelengths such as those in the infrared can disadvantageously overheat the algae, thereby decreasing the efficiency of their growth.

Thus, embodiments described herein are directed to solar-redshift modules and to solar-redshift systems that may be constructed from either an integral array of solar-redshift modules or a parallel-plate configuration of solar-redshift modules. The solar-redshift modules may include at least one collecting target having a target wavelength, at least one quantum-dot vessel, and a focusing device that focuses incident solar radiation into the solar redshift system. In general, the at least one collecting target of a solar-redshift module may be selected from a growth vessel or a photovoltaic plate. These solar-redshift modules may be incorporated into solar-redshift systems such as, for example, a photovolatic solar-redshift system including only photovolatic solar-redshift modules with photovoltaic plates as collecting targets, as photosynthesis-enhancing solar-redshift systems including only photosynthesis-enhancing solar-redshift modules with growth vessels as collecting targets, or hybrid systems containing some photovolatic solar-redshift modules and some photosynthesis-enhancing solar-redshift modules.

In solar-redshift modules including a growth vessel as a collecting target (i.e., photosynthesis-enhancing solar-redshift modules), the growth vessel may contain a living photosynthetic organism in a growth medium for sustaining the living photosynthetic organism, such that the target wavelength is a wavelength of increased photosynthetic response of the living photosynthetic organism. In solar-redshift modules including a photovoltaic plate as a collecting target (i.e., photovolatic solar-redshift modules), the photovolatic plate may include a photovoltaic material, such that the target wavelength is a wavelength of increased sensitivity of the photovoltaic material. Regardless of the type of solar-redshift module present in the solar-redshift system, however, the focusing device, the at least one quantum-dot vessel, and the at least one collecting target may be configured such that the incident solar radiation focused into the solar redshift system strikes the at least one quantum-dot vessel before striking the at least one collecting target. Thus, the light that strikes the collecting target is never incident solar radiation directly from the sun but, rather, is light that is at least substantially enriched in the target wavelength of the collecting target.

Figure 1B:
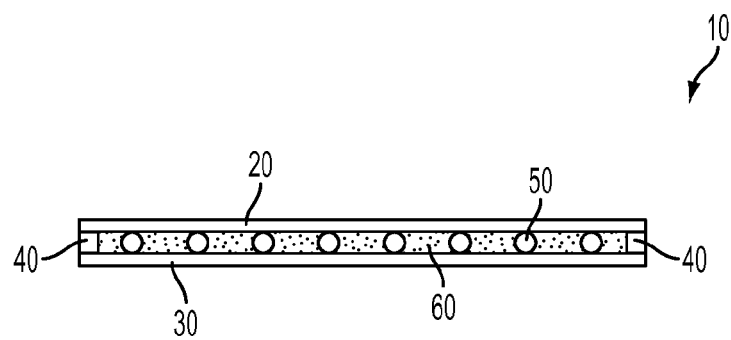
FIG. 1B is a cross-sectional side view of the quantum-dot vessel shown in FIG. 1A.

Quantum-dot vessels and methods for their construction now will be described with reference to FIGS. 1A and 1B, which show a non-limiting embodiment of a quantum-dot vessel 10. FIG. 1A is a top plan view of the quantum-dot vessel 10, and FIG. 1B is a cross-sectional side view of the quantum-dot vessel 10 of FIG. 1A. The quantum-dot vessel 10 may comprise a first plate 20 and a second plate 30. Though the first plate 20 and the second plate 30 are shown in FIG. 1A to be square or rectangular, it should be understood that the first plate 20 and the second plate 30 may have a desirable shape, according to the needs of the application involved. For example, the quantum-dot vessel 10 may be a long bar having a narrow width and a very long length or may be circular or another desired geometric shape.

Actual dimensions of the quantum-dot vessel 10 may be chosen according to needs of the energy-harvesting application. It is contemplated that the quantum-dot vessel 10 may have length and width dimensions independently ranging from about 1 mm to about 100 m, in some of these embodiments from about 1 cm to about 10 m, and in some of these embodiments from about 10 cm to about 2 m. Also, though the first plate 20 and the second plate 30 are shown to be flat, it should be understood that the plates need not necessarily be flat. Though flat plates are particularly advantageous, because they provide a maximum surface area for transmitting redshifted light, variations such as convexly or concavely curved plates are contemplated as alternatives. As a further alternative, the plates may be essentially flat except around edges, and the edges may be curved or bent so as to facilitate sealing the plates together.

The first plate 20 and the second plate 30 may be essentially the same size, as shown in FIG. 1A, or different sizes. For example, the first plate 20 can be smaller than the second plate 30, such that the quantum-dot vessel 10 will have a trapezoidal cross-section instead of the rectangular cross-section shown in FIG. 1B. The first plate 20 and the second plate 30 are separated, in the embodiment shown, by separator structures 50 such as glass beads or pillars. For example, the separator structures 50 may be glass microspheres, such that when the separator structures 50 are sandwiched between the first plate 20 and the second plate 30, a gap of from about 50 µm to about 500 µm, or in some embodiments from about 100 µm to about 350 µm, or in other embodiments from about 150 µm to about 250 µm is formed. The glass microspheres in some embodiments have minimal variance in diameters, so as to ensure consistent separation of the first plate 20 and the second plate 30, as well as to ensure a constant optical-path length through all portions of the quantum-dot vessel 10.

The first plate 20 and the second plate 30 may be sealed together, for example, along sealing edge 40, such that the first plate 20, the second plate 30, and the sealing edge 40 together define a sealed cavity 60 between the first plate 20 and the second plate 30. Sealing of the sealing edge 40 may be accomplished by a practical means such as, for example, frit sealing, wherein the sealed cavity 60 may be hermetically sealed. Hermetic sealing of the sealed cavity 60 in various embodiments can be selected because many types of quantum dots are extremely sensitive to oxygen, humidity, and other environmental factors. Thus, the hermetic sealing may prevent premature degradation of the quantum dots.

An example method for manufacturing the quantum-dot vessel 10 may comprise frit sealing the first plate 20 and the second plate 30 around the outer perimeter of the plates except at opposing corners, as illustrated in FIG. 1A, with the plates separated with the separator structures 50. Quantum dots may be dispersed within a suitable suspension medium, described below, and the resulting quantum-dot dispersion may be placed in a quantum-dot loader 70. The quantum-dot loader 70 may be fit to the quantum-dot vessel 10, for example, at a loading port 72 located at one of the opposing corners that were not frit sealed. Thereupon, means such as a vacuum pump 75 may be attached to a vacuum port 77 of the quantum-dot vessel 10, such that when the vacuum pump 75 is activated, the quantum dots in the suspension medium are drawn from the quantum-dot loader 70 and into the sealed cavity 60. Once the sealed cavity 60 is filled with quantum dots, the unsealed corners at the loading port 72 and the vacuum port 77 of the quantum-dot vessel 10 may be sealed, such that the sealing edge 40 is continuous around the outer perimeter of the quantum-dot vessel 10. To avoid exposure of the quantum dots to oxygen during the filling process, the quantum-dot vessel 10 in some embodiments is filled in an inert environment such as in a nitrogen or an argon controlled atmosphere.

The quantum dots to be loaded into the quantum-dot vessel 10 may be any known or to-be-discovered type of quantum dot formed using any appropriate technique. It is readily known to those skilled in the art that one requiring quantum dots for a certain application may specify a desired emission wavelength and a selected material, with which information a supplier can readily determine from known information the quantum-dot size to produce quantum dots of the selected material and having the desired emission wavelength.

The material from which the quantum dots are made may include, as non-limiting examples: MgO; MgS; MgSe; MgTe; CaO; CaS; CaSe; CaTe; SrO; SrS; SrSe; SrTe; BaO; BaS; BaSe; BaTe; ZnO; ZnS; ZnSe; ZnTe; CdO; CdS; CdSe; CdTe; HgO; HgS; HgSe; HgTe; $Al_2O_3$; $Al_2S_3$; $Al_2Se_3$; $Al_2Te_3$; $Ga_2O_3$; $Ga_2S_3$; $Ga_2Se_3$; $Ga_2Te_3$; $In_2O_3$; $In_2S_3$; $In_2Se_3$; $In_2Te_3$; $SiO_2$; $GeO_2$; $SnO_2$; SnS; SnSe; SnTe; PbO; $PbO_2$; PbS; PbSe; PbTe; AlN; AlP; AlAs; AlSb; GaN; GaP; GaAs; GaSb; InN; InP; InAs; InSb; and ternary, quaternary, and higher alloys of any of the preceding materials including, but not limited to InGaP, AlInN, CuInGaS, CuInGaSe ("CIGS"), ZnCuInGaS, and (Al,In,Ga)(N,P,As). It is contemplated also that the quantum dots may comprise so-called core-shell structures, wherein individual quantum dots are made from a core of one of the above-listed materials and the core is surrounded by a shell of another of the above-listed materials.

The material chosen as the quantum dot material can be tailored through selection of quantum-dot size to emit a wavelength of light useful to a particular energy-harvesting application when the quantum dots are illuminated with incident solar radiation. As used herein, the term "quantum-dot size" refers to an average diameter of quantum dots taken over all quantum dots present in the quantum-dot vessel 10. For example, a quantum dot made of $CdS_xSe_{1-x}$ ($0 \leq x \leq 1$) or ZnS with a quantum-dot size of from about 5.5 nm to about 6.5 nm will emit light having a wavelength of about 680 nm, a wavelength that enhances photosynthesis in certain species of algae. Likewise, a quantum dot made of CdSe with a quantum-dot size of from about 3.6 nm to about 4.6 nm will emit light having a wavelength of about 600 nm, a wavelength desirable for photovoltaic applications involving CdTe or CIGS as a photovoltaic material, for example.

The quantum dots may be contained within the quantum-dot vessel 10 in the form of a quantum-dot suspension or a functionalized matrix. The quantum-dot suspension or functionalized matrix may be formed by dispersing the quantum dots in a suspension medium, which subsequently may be loaded into the quantum-dot vessel 10. The suspension or functionalized matrix may comprise a suitable suspension medium, examples of which are disclosed in U.S. Pat. App. Pub. No. 2010/0276638 to Liu, et al., which document is incorporated herein by reference in its entirety. In general, the suspension medium is a functionalized polymer, typically in liquid form. The suspension medium optionally may be crosslinked by heat, for example, once the quantum dots are added. When contained within the quantum-dot vessel 10, the quantum-dot suspension is a liquid, a gel, or a solid; in one group of embodiments, the quantum-dot suspension is a gel or a solid. The suspension medium serves primarily to maintain physical separation among the quantum dots within the quantum-dot vessel 10, and also to prevent agglomeration of the quantum dots within the quantum-dot vessel 10. Separation and lack of agglomeration of the quantum dots ensures efficient exposure of the quantum dots to incident solar radiation and further may increase conversion efficiency of the incident solar radiation to redshifted light having the desired wavelengths.

In view of the general description above, pertaining to features generally common to embodiments of solar-redshift systems that will be described below, various illustrative configurations of solar-redshift systems now will be described. Initially, embodiments of gap-focus configurations will be described. The gap-focus configurations have in common that the focusing device focuses incident solar radiation through a focusing gap, after which the incident solar radiation is directed to a quantum-dot vessel and then to the collecting target. Illustrative embodiments of the gap-focus configurations include a gap-to-reflector configuration and a gap-to-vessel configuration. First, in illustrative embodiments, photovoltaic solar-redshift modules and photovoltaic solar-redshift systems having the gap-to-reflector configuration will be described with reference to FIGS. 2, 3A, and 3B. Second, in illustrative embodiments, photosynthesis-enhancing solar-redshift modules and photosynthesis-enhancing solar-redshift systems having the gap-to-vessel configuration will be described with reference to FIGS. 4 and 5. It should be noted that both of the gap-focus configurations may be employed equally well as bases for photovoltaic solar-redshift systems, for photosynthesis-enhancing solar-redshift systems, or hybrid solar-redshift systems. Thus, it should be understood that the general descriptions of photovoltaic solar-redshift systems in gap-to-reflector configurations and of photosynthesis-enhancing solar-redshift systems in gap-to-vessel configurations are not intended to be limiting. Third, embodiments of parallel-plate solar-redshift systems having parallel-plate configurations will be described with reference to FIGS. 6-11. The illustrative embodiments of the parallel-plate solar-redshift systems are photosynthesis-enhancing solar-redshift systems. Even so, similar to the gap-focus configurations, the parallel-plate configuration can be adapted for use in photovoltaic solar-redshift systems, photosynthesis-enhancing solar-redshift systems, or combination system.

An illustrative embodiment of a solar-redshift module (e.g., a photovoltaic solar-redshift module) having a gap-to-reflector configuration is provided in FIG. 3B and will be described below as a component of the photovoltaic solar-redshift system 100 of FIG. 2. The gap-to-reflector configuration in general is arranged such that a focusing device 160 focuses the incident solar radiation following the incident-radiation optical path 155 through a focusing gap 190 between a first quantum-dot vessel 10*a* and a second quantum-dot vessel 10*b* toward a plate reflector 180. The plate reflector 180 reflects the light to the quantum-dot vessels 10*a*, 10*b*, wherein the light is redshifted before ever encountering the collecting target (for example, photovoltaic plate 170 in FIG. 3B). It should be understood that the photovoltaic solar-redshift system 100 of FIG. 2 is but one embodiment of a system including solar-redshift modules having the gap-to-reflector configuration and that in other embodiments the gap-to-reflector configuration may be used in a photosynthesis-enhancing solar redshift system (to be described below in further detail) by substituting a growth vessel as the collecting target in the place of the photovoltaic plate 170.

Figure 2:
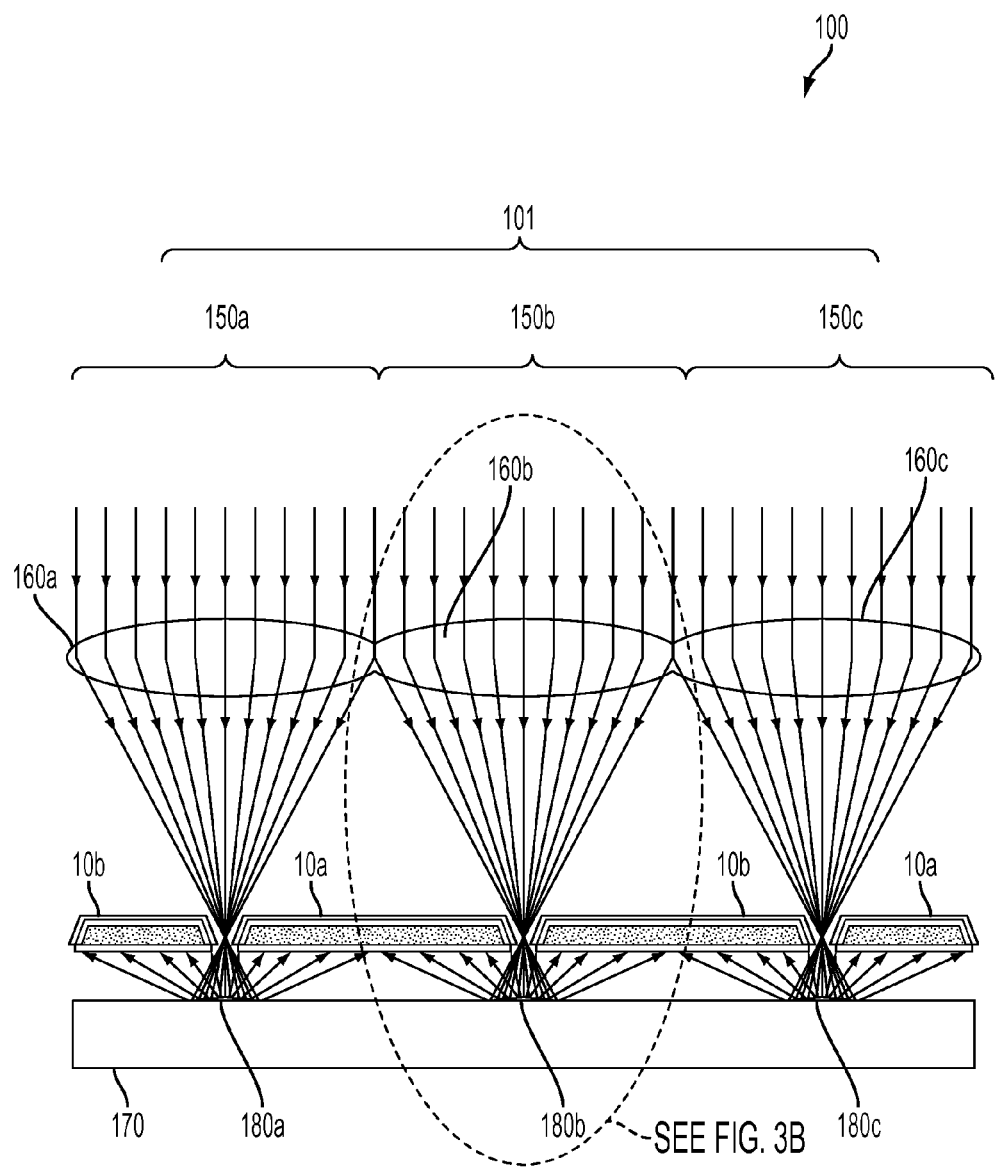
FIG. 2 is a solar-redshift system according to illustrative embodiments described herein, which has a gap-to-reflector configuration including an integral array of photovoltaic solar-redshift modules, each of which includes a quantum-dot vessel.

Referring to FIG. 2, an embodiment of a photovoltaic solar-redshift system 100 is provided as an example of a solar-redshift system having the gap-to-reflector configuration. The photovoltaic solar-redshift system 100 may comprise an integral array 101. As used herein, the term "integral array" refers to a continuous system having repeating modular structures, wherein each of the modular structures is physically connected to at least one neighboring modular structure. Typically, each modular structure is physically connected to one or two neighboring structures in a one-dimensional array, or from one to four neighboring modular structures in a two-dimensional array.

The integral array 101 is made up of repeating units defined as the photovoltaic solar-redshift modules 150*a*, 150*b*, 150*c*. Though, for sake of clarity, the integral array 101 of FIG. 2 includes only three of the photovoltaic solar-redshift modules 150*a*, 150*b*, 150*c*, it should be understood that the integral array 101 may comprise any desired number of photovoltaic solar-redshift modules, for example, up to several million, from 2 to 100,000, from 5 to 50,000, or from 10 to 10,000. Likewise, it should be understood that the integral array 101 in FIG. 2 is shown effectively in cross-section as a one-dimensional array, and that, in practice, the integral array 101 may extend in a second dimension, into or out of the plane of FIG. 2, so as to harvest energy from incident solar radiation falling on a large surface area, e.g. of land.

Each of the photovoltaic solar-redshift modules 150*a*, 150*b*, 150*c* comprises a photovoltaic plate 170; a first quantum-dot vessel 10*a*; a second quantum-dot vessel 10*b*; a plate reflector 180*a*, 180*b*, 180*c*, respectively; and a focusing device 160*a*, 160*b*, 160*c*, respectively. Though FIG. 2 shows the photovoltaic plate 170 in the photovoltaic solar-redshift system 100 as a single, continuous piece of photovoltaic material, it should be understood that additional configurations are possible, wherein each of the photovoltaic solar-redshift modules 150*a*, 150*b*, 150*c* may comprise a separate piece of photovoltaic material. It should be understood that the photovoltaic plate may further comprise electrical contacts (not shown) electrically connected in a practical manner to a device such as an energy storage system (not shown) or a power delivery system (not shown). Likewise, though in FIG. 2 the focusing device 160*a*, 160*b*, 160*c* of each of the photovoltaic solar-redshift modules 150*a*, 150*b*, 150*c*, respectively, is depicted as part of an integral array of converging lenses, this configuration is to be understood as an example by way of illustration, not of limitation. It should be understood that numerous additional optical configurations and devices are possible. For example, as alternatives to the integral array of converging lenses, separate individual lenses may be used. Furthermore, other optical devices capable of directing rays of incident solar radiation may be used, such as for example, appropriately designed mirrors or solar collectors such as solar troughs.

It should be understood by the skilled person that variations in the direction of incident solar radiation relative to the focusing device 160*a*, 160*b*, 160*c* of each of the photovoltaic solar-redshift modules 150*a*, 150*b*, 150*c*, respectively, will occur over the course of a single day and also during the course of the year. Generally, the position of the sun in the sky may be expressed as polar coordinates that include an azimuth and an elevation. The azimuth coordinate is typically expressed as a bearing, with due north being 0° or 360°, due east being 90°, due south being 180°, and due west being 270°. Given the azimuth coordinate, the elevation coordinate allows an observer who first orients toward the azimuth to look up in the sky to a particular angle to find the sun. For the elevation coordinate, toward the horizon is defined as 0° elevation, and toward the zenith (directly overhead) is defined as 90° elevation.

For solar-collection systems such as, but not limited to, the solar-redshift systems described herein, variations over the course of a day arise from the movement of the sun across the sky from east to west and typically may be addressed by azimuthal single-axis tracking. Variations over the course of a year arise from the 23.5° angle of the earth's rotation axis relative to the plane of the earth's orbit and typically may be addressed by elevational single-axis tracking. To account for both daily and yearly variations in the direction of incident solar radiation may require dual-axis tracking.

Though mechanisms for single-axis tracking or dual-axis tracking are not shown in FIG. 2, it is fully contemplated that the photovoltaic solar-redshift system 100 may further comprise such mechanisms. In one exemplary embodiment, a suitable mechanism may be incorporated that widens the focusing gaps 190 of the photovoltaic solar-redshift modules 150 over the course of the year, thereby reducing or eliminating any need for large-scale dual-axis tracking mechanisms such as those that may require constantly adjusting the inclination of the entire photovoltaic solar-redshift system 100 over the course of a year. In such an embodiment, a wider focusing gap 190 may permit incident solar radiation arriving at the focusing device 160 at a steeper angle (in winter compared to in summer, for example) to continue being focused through the focusing gap 190 over the course of a year without otherwise adjusting the inclination of the entire photovoltaic solar-redshift system 100. This gap-widening principle could then be used in combination with an azimuthal single-axis tracking mechanism that adjusts the photovoltaic solar-redshift system 100 over the course of a day, such that the photovoltaic solar-redshift system 100 would provide the advantages of dual-axis tracking with the only the gross infrastructure of a single-axis tracking system. It should be noted, however, that widening the focusing gap 190 in this manner may also result in increased loss, owing to a heightened ability for reflected or redshifted light to escape back out through the focusing gap 190 without striking the quantum-dot vessels 60a, 60b or the photovoltaic plate 170.

Figure 3A:
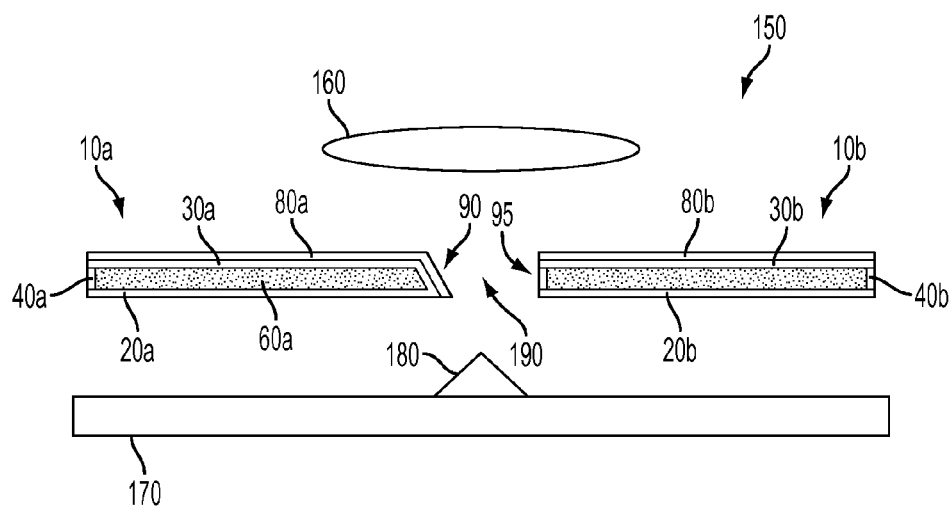
FIG. 3A is a solar-redshift module according to embodiments described herein and forming a component of the solar-redshift system of FIG. 2, highlighting structural features that repeat within the integral array.
Figure 3B:
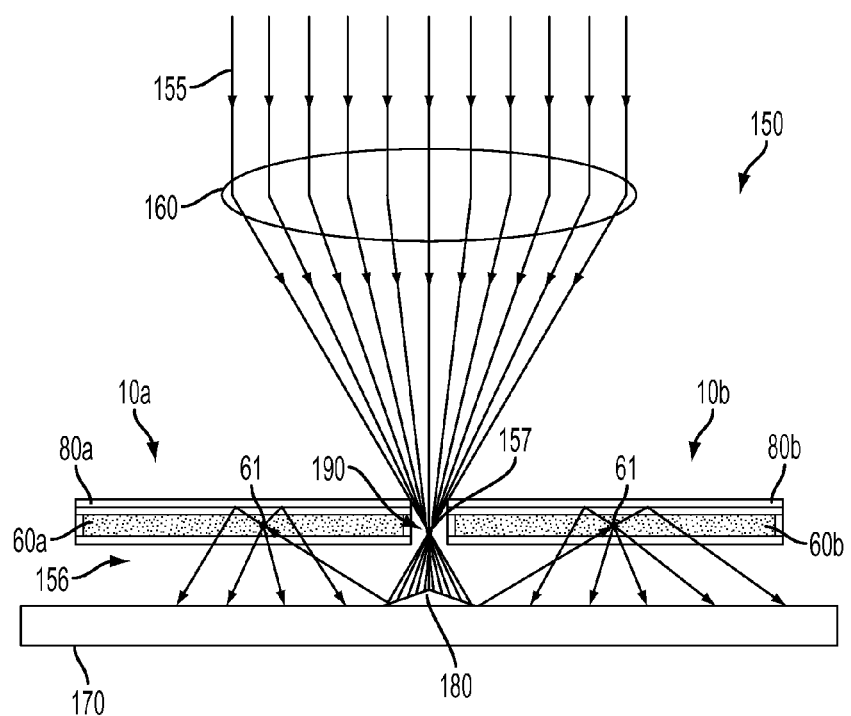
FIG. 3B is the solar-redshift module from FIG. 3A, illustrating via ray tracings the pathways of incident solar radiation and redshifted light within the solar-redshift module.

A photovoltaic solar-redshift module 150, isolated from the integral array 101 shown in FIG. 2 to illustrate specific details, is described now with reference to FIGS. 3A and 3B. The photovoltaic solar-redshift module 150 comprises a photovoltaic plate 170, a first quantum-dot vessel 10a, a second quantum-dot vessel 10b, a plate reflector 180, and a focusing device 160. The first quantum-dot vessel 10a and the second quantum-dot vessel 10b are interposed between the focusing device 160 and the photovoltaic plate 170 along an incident-radiation optical path 155.

The photovoltaic plate 170 comprises a photovoltaic material having at least one wavelength of increased sensitivity. As used herein, the "sensitivity" of a photovoltaic material to a given wavelength of incident electromagnetic radiation refers to the efficiency by which the photovoltaic material converts the electromagnetic radiation to an electrical potential. A wavelength of light to which a given photovoltaic material is more sensitive (i.e., has a higher quantum efficiency for producing an electrical potential in the photovoltaic material) than to others is defined herein as a property inherent to the photovoltaic material itself, namely, as a "wavelength of increased sensitivity" of the photovoltaic material. Thus, the term "a photovoltaic material having at least one wavelength of increased sensitivity" is equivalent to stating that the photovoltaic material is more sensitive to one particular wavelength (i.e., the wavelength of increased sensitivity) than it is to other wavelengths.

Generally, photovoltaic materials are characterized in that they produce an electric potential when exposed to incident electromagnetic radiation. The effective quantum efficiency of a photovoltaic material, an increase of which correlates to the magnitude of the electric potential, typically is a function of the wavelengths of light present in the incident electromagnetic radiation. The response of photovoltaic materials to electromagnetic radiation typically varies with respect to the wavelength of the electromagnetic radiation incident on the photovoltaic material, such that each photovoltaic material is more sensitive to certain wavelengths than to others.

In view of the above definitions, a given photovoltaic material may possess one wavelength of increased sensitivity or multiple wavelengths of increased sensitivity, because the response of the given photovoltaic material varies with respect to wavelength of light incident on the photovoltaic material. The given photovoltaic material also may possess at least one wavelength of optimal sensitivity. In quantitative terms, a wavelength of increased sensitivity may be defined further as any wavelength of incident light that results in an effective quantum efficiency in the photovoltaic material that is higher, in some embodiments at least 10% higher, in some embodiments at least 25% higher, or in some embodiments at least 50% higher, than the lowest effective quantum efficiency achieved from exposing the photovoltaic material to monochromatic light of each wavelength in the visible spectrum (from about 380 nm to about 750 nm). The wavelength of optimal sensitivity is defined herein as the wavelength of incident light in the visible spectrum that results in the highest effective quantum efficiency for producing an electric potential in the photovoltaic material.

The photovoltaic plate 170 may be formed from or may comprise at least one photovoltaic material. The photovoltaic material may be any known or to-be-discovered photovoltaic material. Examples of known photovoltaic materials suitable for use in the photovoltaic plate 170 include, but are not limited to: Si, $CuInSe_2$, MgO; MgS; MgSe; MgTe; CaO; CaS; CaSe; CaTe; SrO; SrS; SrSe; SrTe; BaO; BaS; BaSe; BaTe; ZnO; ZnS; ZnSe; ZnTe; CdO; CdS; CdSe; CdTe; HgO; HgS; HgSe; HgTe; $Al_2O_3$; $Al_2S_3$; $Al_2Se_3$; $Al_2Te_3$; $Ga_2O_3$; $Ga_2S_3$; $Ga_2Se_3$; $Ga_2Te_3$; $In_2O_3$; $In_2S_3$; $In_2Se_3$; $In_2Te_3$; $SiO_2$; $GeO_2$; $SnO_2$; F-doped $SnO_2$ ($SnO_2$:F); SnS; SnSe; SnTe; PbO; $PbO_2$; PbS; PbSe; PbTe; AlN; AlP; AlAs; AlSb; GaN; GaP; GaAs; GaSb; InN; InP; InAs; InSb; ternary, quaternary, and higher alloys of any of the preceding materials including, but not limited to InGaP, AlInN, CuInGaS, CuInGaSe ("CIGS"), ZnCuInGaS, (Al,In,Ga)(N,P,As), and $(Cu,Ag,Au)(Al,Ga,In)(S,Se,Te)_2$; and even organic photovoltaic materials such as squarylium and cyanine-TCNQ compounds. The photovoltaic material may be a bulk material or may be a coating or functional layer deposited on an appropriate substrate such as silicon. In the formulas of photovoltaic cells including parentheses, one, two, or three of the elements in each set of parentheses may be included in the compound.

The first quantum-dot vessel 10a and the second quantum-dot vessel 10b may be, but need not be, geometrically or structurally identical. Nevertheless, the quantum-dot vessels 10a, 10b both comprise identical functional components, even if the functional components are configured slightly differently, such as with respect to geometry or cross-section. Thus, structural features of the quantum-dot vessels will be described with reference to only the first quantum-dot vessel 10a, with the understanding that second quantum-dot vessel 10b comprises corresponding structural features. Referring jointly to FIGS. 3A and 3B, the first quantum-dot vessel 10a comprises a sealed cavity 60a defined between a first plate 20a and a second plate 30a. The first plate 20a and the second plate 30a may be hermetically sealed, as described above with reference to FIGS. 1A and 1B, about a sealing edge 40a. Thus, a sealed cavity 60a is defined between the first plate 20a and the second plate 30a.

In the first quantum-dot vessel 10a, a quantum-dot suspension is disposed within the sealed cavity 60a. The quantum-dot suspension comprises quantum dots suspended in a suspension medium. The quantum dots are formed of a quantum-dot material and have a quantum-dot size, wherein the quantum dots emit a redshifted light 156 having the wavelength of increased sensitivity when the quantum dots are irradiated by incident solar radiation. As such, a synergy is present between the emission wavelength of the quantum dots and the wavelength of increased sensitivity of the photovoltaic material in the photovoltaic plate 170. Suitable quantum-dot materials, quantum-dot sizes, and suspension media, are as described above with reference to the quantum dot vessel 10 of FIGS. 1A and 1B.

The first quantum-dot vessel 10a and the second quantum-dot vessel 10b are configured between the photovoltaic plate 170 and the focusing device 160 such that a focusing gap 190 is defined between the first quantum-dot vessel 10a and the second quantum-dot vessel 10b. The size of the focusing gap 190 is defined, in particular, by the shortest distance between first gap edge 90 of the first quantum-dot vessel 10a and the second gap edge 95 of the second quantum-dot vessel 10b. The first gap edge 90 and the second gap edge 95 may have a desired profile, which may be the same or different from one another, and of which two non-limiting examples are shown in FIG. 3A. Namely, first gap edge 90 is shown as sloping inwardly, such that the focusing gap 190 narrows in a direction from the focusing device 160 toward the photovoltaic plate 170 and is narrowest adjacent to the first plate 20a of the first quantum-dot vessel 10a, i.e., the closest point within the focusing gap 190 to the photovoltaic plate 170. Alternatively, the second gap edge 95 is shown as perpendicular to the first plate 20b of the second quantum-dot vessel 10b. Gap edges, such as shown for first gap edge 90, may be advantageous because a narrower width of the focusing gap 190 may decrease losses of incident solar radiation upwardly through the focusing gap 190, such as may occur when the incident solar radiation reflects off the photovoltaic plate 170.

Referring specifically to FIG. 3B, the focusing device 160 is an optical apparatus that directs incident solar radiation along the incident-radiation optical path 155 (referring to the entire ray tracing from above the focusing device 160 until the rays enter the first quantum-dot vessel 10a or the second quantum dot vessel 10b) through the focusing gap 190 and onto the plate reflector 180. As noted above, the focusing device 160, though depicted in FIG. 3B as a converging lens, may be selected from any appropriate optical device having an equivalent function, namely, an optical device that can direct the incident solar radiation through the focusing gap 190. Alternative devices in this regard include, for example, converging mirrors, or solar collectors such as troughs. The plate reflector 180 is disposed on a surface of the photovoltaic plate 170 and reflects the incident solar radiation toward at least one of the quantum dot vessels (here, the first quantum-dot vessel 10a or the second quantum-dot vessel 10b). Note that, for clarity, only two ray paths on each side of the plate reflector 180 are shown in FIG. 3B. It should be readily ascertainable from the geometric configuration of the plate reflector 180 in the example shown in FIG. 3B that light rays incident on the plate reflector 180 will be reflected toward one of the quantum-dot vessels 10a, 10b.

In FIG. 3B, as a non-limiting example, the focusing device 160 is shown as a converging lens arranged with respect to the focusing gap 190 such that a focal point 157 of the focusing device 160, representing the narrowest width of the incident radiation optical path 155, is disposed within the focusing gap 190 itself. As such, in some embodiments the width of the focusing gap 190 can be intentionally chosen as equal to, or nearly equal to, the width of the focal point 157 of the focusing device 160. However, maintaining the position of the focal point 157 at a fixed location within the focusing gap 190 may require additional means such as single-axis tracking or dual-axis tracking, described above. Nevertheless, the configuration shown in FIG. 3B may decrease or eliminate the need generally for dual-axis tracking, provided the focusing gap 190 is sufficiently wide to allow incident solar radiation to pass through the focusing gap 190 at all months of the year without unacceptably decreasing the intensity of light hitting the plate reflector 180.

The plate reflector 180 reflects the incident solar radiation toward at least one of the quantum-dot vessels 10a, 10b. The plate reflector 180 may be reflective of all wavelengths or of only selected wavelengths. As such, the plate reflector 180 may be, for example, a silvered mirror, a shiny or polished metal, or a painted surface such as a surface painted white. In one group of embodiments, the plate reflector 180 is a shiny or polished metal such as aluminum, stainless steel, or silver, for example. In some embodiments, the profile of the plate reflector 180 is chosen such that upward reflection of any portion of the incident solar radiation back through the focusing gap 190 is minimized or avoided entirely.

When the incident solar radiation enters the quantum-dot vessels 10a, 10b and contacts the quantum dots therein, redshifted light 156 is emitted from the quantum dots in all directions, including upward and away from the photovoltaic plate 170. This effect is illustrated in FIG. 3B within the first quantum-dot vessel 10a and the second quantum-dot vessel 10b where the light rays intersecting the quantum dot suspension at reference point 61. Thus, each of the quantum-dot vessels 10a, 10b in each photovoltaic solar-redshift module 150 and, referring to FIG. 2, in the integral array 101, comprises a trapping reflector 80a, 80b that reflects at least a portion of said redshifted light 156 toward the photovoltaic plate 170. Specifically, the trapping reflector 80a, 80b reflects the portion of redshifted light 156 that is emitted upwardly, away from the photovoltaic plate 170. Without the trapping reflector 80a, 80b, some redshifted light 156 of the most desirable wavelengths for the energy-harvesting application involved with the photovoltaic solar-redshift system 100 may be lost without benefiting the system.

The trapping reflector may be, for example, a coating on any surface of the second plate 30a, 30b of the quantum-dot vessels 10a, 10b or, as a further example, a reflective object contacting the sunward surface of the second plate 30a, 30b in a manner that prevents escape of redshifted light 156. Additionally, the trapping reflector 80a, 80b may be reflective to the wavelength of the redshifted light 156 yet transmissive of other wavelengths of light. Thus, the trapping reflector 80a, 80b ensures not only that the most desirable wavelengths of redshifted light 156 are produced by emission from the quantum dots, but also that losses of redshifted light 156 due to upward reflection are minimized or prevented entirely.

Having described various embodiments of a gap-to-reflector configuration of a solar-redshift system, particularly with exemplary reference to the photovoltaic solar-redshift systems using photovoltaic plate 170 as a collecting target, now additional solar-redshift systems having a gap-to-vessel configuration will be described. An illustrative embodiment of a solar-redshift module (e.g., a photosynthesis-enhancing solar-redshift module) having a gap-to-reflector configuration is provided in FIG. 5 and will be described below as a component of the photosynthesis-enhancing solar-redshift system 200 of FIG. 4. The gap-to-vessel configuration in general is arranged such that a focusing device 160 focuses the incident solar radiation following the incident-radiation optical path 155 through a focusing gap 290 directly onto the quantum-dot vessel 10, wherein the incident solar radiation is redshifted before ever encountering a collecting target (e.g., first growth vessel 270a or second growth vessel 270b). Whereas in the gap-to-reflector configuration, a focusing gap 190 (FIG. 3B) is defined between two quantum-dot vessels 10a, 10b (FIG. 3B), in the gap-to-vessel configuration, the focusing gap 290 is defined between two separate collecting targets (e.g., first growth vessel 270a and the second growth vessel 270b). It should be understood that the photosynthesis-enhancing solar-redshift system 200 of FIG. 4 is but one embodiment of a system including solar-redshift modules having the gap-to-vessel configuration and that in other embodiments the gap-to-vessel configuration may be used in a photovoltaic solar redshift system by substituting photovoltaic plates as the collecting target in the place of the growth vessels 270a, 270b.

Figure 4:
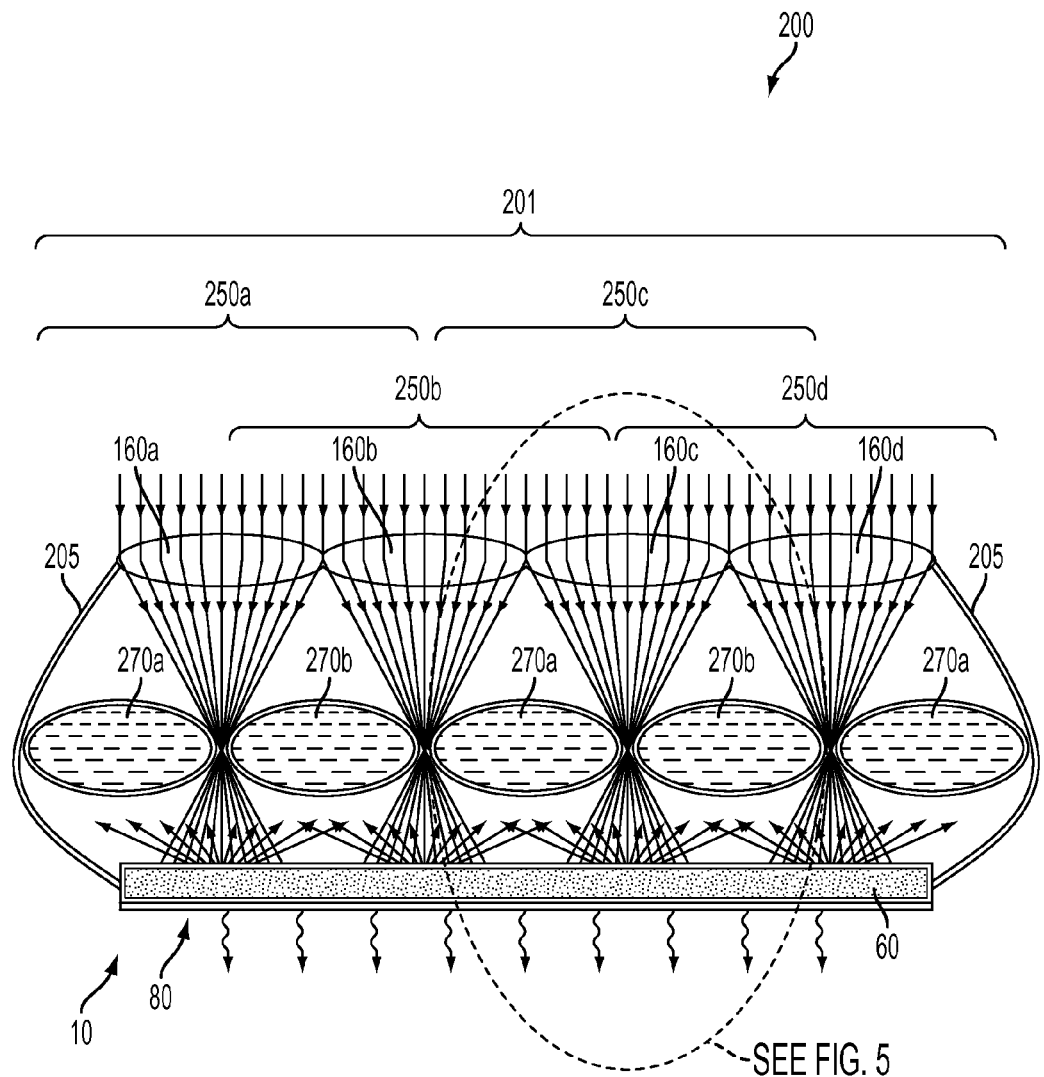
FIG. 4 is a solar-redshift system according to illustrative embodiments described herein, which has a gap-to-vessel configuration including an integral array of photosynthesis-enhancing solar-redshift modules with shared quantum-dot vessels.

Referring to FIG. 4, an embodiment of a photosynthesis-enhancing solar-redshift system 200 is provided as an example of a solar-redshift system having the gap-to-vessel configuration. Analogous to the photovoltaic solar-redshift system 100 (see FIG. 2), the photosynthesis-enhancing solar-redshift system 200 comprises an integral array 201. The integral array 201 can be made up of repeating units defined as photosynthesis-enhancing solar-redshift modules. Four photosynthesis-enhancing solar-redshift modules 250a, 250b, 250c, 250d are shown in FIG. 4. Though, for sake of clarity, the integral array 201 shown in FIG. 4 includes only four of the photosynthesis-enhancing solar-redshift modules 250a, 250b, 250c, 250d, it should be understood that the integral array 201 may comprise any desired number of photosynthesis-enhancing solar-redshift modules, for example, up to several million, from 2 to 100,000, from 5 to 50,000, or from 10 to 10,000. Likewise, it should be understood that the integral array 201 in FIG. 4 is shown effectively in cross-section as a one-dimensional array, and that, in practice, the integral array 201 may extend in a second dimension, into the plane of FIG. 4, so as to harvest energy from incident solar radiation falling on a large surface area of land. The integral array 201 may be an open system or may be a component of a larger apparatus such as a closed bioreactor (not shown).

The photosynthesis-enhancing solar-redshift system 200 optionally may comprise system walls 205 containing some or all of the components of the photosynthesis-enhancing solar-redshift modules 250a, 250b, 250c, 250d. The system walls 205 may be provided, for example, to prevent dirt or other contaminants from adversely affecting optical transmission through various components of the photosynthesis-enhancing solar-redshift modules 250a, 250b, 250c, 250d. The system walls 205, when present, also may act as reflectors to prevent escape of stray light from the portion of the photosynthesis-enhancing solar-redshift system 200 enclosed within the system walls 205.

Each of the photosynthesis-enhancing solar-redshift modules 250a, 250b, 250c, 250d comprises a quantum-dot vessel 10; a focusing device 160a, 160b, 160c, 160d, respectively; a first growth vessel 270a, and a second growth vessel 270b. Though FIG. 4 shows the quantum-dot vessel 10 in the photosynthesis-enhancing solar-redshift system 200 as a single, continuous quantum-dot vessel, it should be understood that additional configurations are possible, wherein each of the photosynthesis-enhancing solar-redshift modules 250a, 250b, 250c, 250d may comprise a separate quantum-dot vessel not physically connected to the quantum-dot vessel of another module. Likewise, though in FIG. 4 the focusing device 160a, 160b, 160c, 160d corresponding to each of the photosynthesis-enhancing solar-redshift modules 250a, 250b, 250c, 250d, respectively, is depicted as part of an integral array of converging lenses, this configuration is to be understood as an example by way of illustration, not of limitation. It should be understood that numerous additional optical configurations and devices are possible. For example, as alternatives to the integral array of converging lenses, separate individual lenses may be used. Furthermore, other optical devices capable of directing rays of incident solar radiation may be used, such as for example, appropriately designed mirrors or solar collectors such as solar troughs.

It should be understood by the skilled person that variations in the direction of incident solar radiation relative to the focusing device 160a, 160b, 160c, 160d corresponding to each of the photosynthesis-enhancing solar-redshift modules 250a, 250b, 250c, 250d, respectively, will occur over the course of a single day and also during the course of the year. Variations over the course of a day arise from the movement of the sun across the sky from east to west and typically may be addressed by azimuthal single-axis tracking. Variations over the course of a year arise from the 23.5° angle of the earth's rotation axis relative to the plane of the earth's orbit typically may be addressed by elevational single-axis tracking. To account for both the daily and yearly variations of the angle of incident solar radiation may require dual-axis tracking.

Though mechanisms for single-axis tracking or dual-axis tracking are not shown in FIG. 4, it is fully contemplated that the photosynthesis-enhancing solar-redshift system 200 may further comprise such mechanisms. In one exemplary embodiment, a suitable mechanism may be incorporated that widens the focusing gaps 290 of the photovoltaic solar-redshift modules 250 over the course of the year, thereby reducing or eliminating any need for large-scale dual-axis tracking mechanisms such as those that may require constantly adjusting the inclination of the entire photosynthesis-enhancing solar-redshift system 200 over the course of a year. In such an embodiment, a wider focusing gap 290 may permit incident solar radiation arriving at the focusing device 160 at a steeper angle (in winter compared to in summer, for example) to continue being focused through the focusing gap 290 over the course of a year without otherwise adjusting the inclination of the entire photosynthesis-enhancing solar-redshift system 200. This gap-widening principle could then be used in combination with an azimuthal single-axis tracking mechanism that adjusts the photosynthesis-enhancing solar-redshift system 200 over the course of a day, such that the photosynthesis-enhancing solar-redshift system 200 would provide the advantages of dual-axis tracking with only the gross infrastructure of a single-axis tracking system. It should be noted, however, that widening the focusing gap 290 in this manner may also result in increased loss, owing to a heightened ability for reflected or redshifted light to escape back out through the focusing gap 290 without striking the quantum-dot vessel 60 or the growth vessels 270a, 270b.

A photosynthesis-enhancing solar-redshift module 250, isolated from the integral array 201 shown in FIG. 4 to illustrate specific details, will be described now with reference to FIG. 5. The photosynthesis-enhancing solar-redshift module 250 comprises a quantum-dot vessel 10, a focusing device 160, a first growth vessel 270a, and a second growth vessel 270b. The first growth vessel 270a and the second growth vessel 270b are interposed between the focusing device 160 and the quantum-dot vessel 10 along an incident-radiation optical path 155.

The first growth vessel 270a and the second growth vessel 270b can be enclosed containers, or conduits (shown in cross-section) such as pipes or tubes, made of materials suitable for growing a photosynthetic organism therein. As used herein, the term "photosynthetic organism" refers to any organism in which photosynthesis occurs as part of a metabolic pathway for sustaining the organism or for causing the organism, or cells thereof, to grow and/or reproduce. Examples of photosynthetic organisms include, without limitation, plants, algae, and photosynthetic bacteria such as cyanobacteria. A "living photosynthetic organism," in contrast with a "dead photosynthetic organism," is any photosynthetic organism in which photosynthesis continues to occur when the organism is exposed to light.

In some embodiments, the living photosynthetic organism may be an organism having utility for producing biomass, wherein the biomass may be burned as a fuel source. In some embodiments, the living photosynthetic organism may be an organism that contains in its body or secretes from its body chemical compounds that can be used, for example, as fuels or as a source for various feedstocks to synthesize bio-derived chemicals or commodities. One highly suitable living photosynthetic organism, as a non-limiting example, is algae. Suitable materials of the first growth vessel 270a and the second growth vessel 270b, when used to enclose growing algae in a liquid medium such as a nutrient-rich algae growth medium include without limitation, for example, glass, acrylic, and various polymers. In some embodiments, such materials are highly transmissive to the wavelengths of light most conducive to photosynthesis by the algae.

Algae that may be used as the living photosynthetic organism in the photosynthesis-enhancing solar-redshift module 250 include, but are not limited to, *Chlorophyta* (green algae), *Charophyta* (Stoneworts and Brittleworts), *Euglenophyta* (Euglenoids), *Chrysophyta* (golden-brown and yellow-green algae and diatoms), *Phaeophyta* (brown algae), *Rhodophyta* (red algae), *Cyanophyta* (blue-green algae, same as blue-green bacteria or cyanobacteria), and the *Pyrrhophyta* (dinoflagellates). In one group of embodiments, the living photosynthetic organism in the photosynthesis-enhancing solar-redshift module 250 include cyanobacteria such as, for example, species *Synechocystis* sp. Most algae are photoautotrophs. As examples of the utility of algae in the photosynthesis-enhancing solar-redshift module 250, most dried algae mass, wet algae colonies, or algae metabolites are known to provide some levels of lipid, saccharidic substances including polysaccharides and sulfated materials (cellulose, hemicellulose, pectin, alginic acid, carrageenan, agarose, porphyran, fucelleran, funoran, starch, simple sugars, and the like), glycoproteins, and a variety of photosynthetic pigments (chlorophyll, astaxanthin, etc) that may be used as a feedstock for bio-derived molecules or bio-derived fuels.

Further suitable species of algae that may be used in the photosynthesis-enhancing solar-redshift module 250 include, but are not limited to; *Actinastnim; Actinochloris; Anabaena; Ankistrodesnnis; Apatococcus; Asterarcys; Auzenochlorella; Bacilliarophy; Botrydiopsis; Botryococcus; Bracteacoccus; Biimilleriopsis; Chaetophora, Chantransia; Charachtm; Chlamydomonas, Chlorella; Chlorideilcr, Chlorobotrys; Chlorococcum; Chlorokybus; Chloroliimula; Chlormonas; Chlorophyceae; Chlorosarcinopsis; Chlorotetraedron; Chloricystis; Coccomyxa; Coelasirella; Coelastropsis; Coelastrum; Coenochloris; Coleochaete; Cosmarium; Crucigenia; Crucigeniella; Desmodesmus; Diadesmis; Dictyococciis; Dictyosphaenum; Dipfosphaera; Dunaliella; Ellipsoidion; Enallax; Ettlia; Euglena; Fortiea; Geminella; Gonium; Graesiella; Haematococcus; Heterococcus; Interfilum; Isochrysis; Kentrosphaera; Keratococcus; Klebsormidium; Koliella; Lagerheimia; Lobosphaera; Macrochloris; Microthamnion; Monodus; Monoraphidium; Mougeotia; Muriella; Mychonastes; Myrmecia; Nannochlolis; Nannochloropsis; Nautococcus; Navicular, Navioua; Neochloris; Neodesmus; Neospongiococcum; Nephrochlamys; Oocystis; Oonephris; Orthotrichum; Pediastrum; Phaeodactylum; Pithophora; Pleurastrum; Pleurochrysis; Porphyridium; Possonia; Prasiolopsis; Protosiphon; Prymnesium, Pseudollipsoidion; Pseudendoclonium; Pseudocharaciopsis; Pseudococcomyxa; Pseudoendoclonium; Raphidocelis; Raphidonema; Rhexinema; Rhopalocystis; Scenedesmus; Schroederiella; Scotiella; Scotiellopsis; Selenastrum, Sphaerocystis; Spirogyra; Spirulina; Spongiochloris; Stichococcus; Stigeoclonium; Synechoccus; Synechocystis sp.; Tetradesmus; Tetrahedron; Tetraselmis; Tetrastrum; Tribonema; Vischeria; Willea; Xanthonema*; and *Zygnema*. These species are known to produce or secrete various lipids, which in turn can be used as precursors to useful bio-derived substances.

The living photosynthetic organism has at least one wavelength of increased photosynthetic response. Analogously to the photovoltaic materials described above, photosynthesis in living photosynthetic organisms, including in the species of algae listed above, progresses with varying rates and/or intensities as a function of the wavelength of light that provides the energy for the photosynthesis. Thus, the term "photosynthetic response" of a living photosynthetic organism at a particular wavelength refers qualitatively to the intensity of photosynthesis that occurs as a result of light having the particular wavelength striking the organism. Photosynthetic response may be ascertained by a known technique, such as by monitoring output of certain metabolites from the organism or by monitoring volume and speed of oxygen production by the organism. A wavelength of light to which a given living photosynthetic organism is more responsive (i.e., has an increased rate of photosynthesis) than to others is defined herein as a property inherent to the living photosynthetic organism itself, namely, as a "wavelength of increased photosynthetic response" of the living photosynthetic organism. Thus, the term "a photosynthetic material having at least one wavelength of increased photosynthetic response" is equivalent to stating that the living photosynthetic organism is more responsive to one particular wavelength (i.e., the wavelength of increased photosynthetic response) than it is to other wavelengths. The term "a photosynthetic material having at least one wavelength of enhanced photosynthetic response" can be used interchangeably with "a photosynthetic material having at least one wavelength of increased photosynthetic response".

In the photosynthesis-enhancing solar-redshift system 200, the quantum dots are selected, with respect to material and quantum-dot size, to emit redshifted light having wavelengths as close as feasible to a wavelength of increased photosynthetic response for the particular algae. Without intent to be limited by theory, it is believed that photosynthesis does not take significant advantage of wavelengths toward the center of the visible, such that redshifting these wavelengths toward a move valuable wavelength would increase photosynthetic growth efficiency. As a non-limiting example, one potential wavelength to target for such a shift is 680 nm (red), which is particularly valuable to photosynthesis. Red is more valuable than green and blue, at least for green plants and green algae, because green light is typically reflected and blue light, though not completely reflected, has a higher energy and, therefore, tends to generate more heat than the red and green light do.

Regardless of the type of living organism present in the photosynthesis-enhancing solar-redshift module 250, the living photosynthetic organism inherently has at least one wavelength of increased photosynthetic response. Likewise, the living photosynthetic organism may have also a wavelength of optimal photosynthetic response. In quantitative terms, a wavelength of increased photosynthetic response may be defined further as any wavelength of incident light that results in a photosynthetic response from the living photosynthetic organism that is higher, in some embodiments at least 10% higher, in some embodiments at least 25% higher, or in some embodiments at least 50% higher, than the lowest photosynthetic response achieved from exposing the organism to monochromatic light of each wavelength in the visible spectrum (from about 380 nm to about 750 nm). As used herein, the wavelength of optimal photosynthetic response is defined as the wavelength of incident light in the visible spectrum that results in the highest photosynthetic response from the living photosynthetic organism.

The growth vessels 270a, 270b may have any suitable shape, size, and wall thickness, and in some embodiments are transparent to at least the wavelengths of increased photosynthetic response of the living photosynthetic organism growing in the growth vessels 270a, 270b. Also, the shape of the growth vessels 270a, 270b can be selected in some embodiments so that surface area directed downward (i.e., toward the quantum-dot vessel 10) is maximized. Thus, the generally ovular shapes presented in the Figures of the growth vessels 270a, 270b are illustrative only, not limiting, and the ovular shapes may be used instead of circular shapes that may not allow redshifted light 156 to pass into the vessels as efficiently.

The first growth vessel 270a and the second growth vessel 270b are configured between the quantum-dot vessel 10 and the focusing device 160 such that a focusing gap 290 is defined between the first growth vessel 270a and the second growth vessel 270b. The size of the focusing gap 290 is defined, in particular, by the shortest distance between the first growth vessel 270a and the second growth vessel 270b, accounting for the respective geometries thereof.

Figure 5:
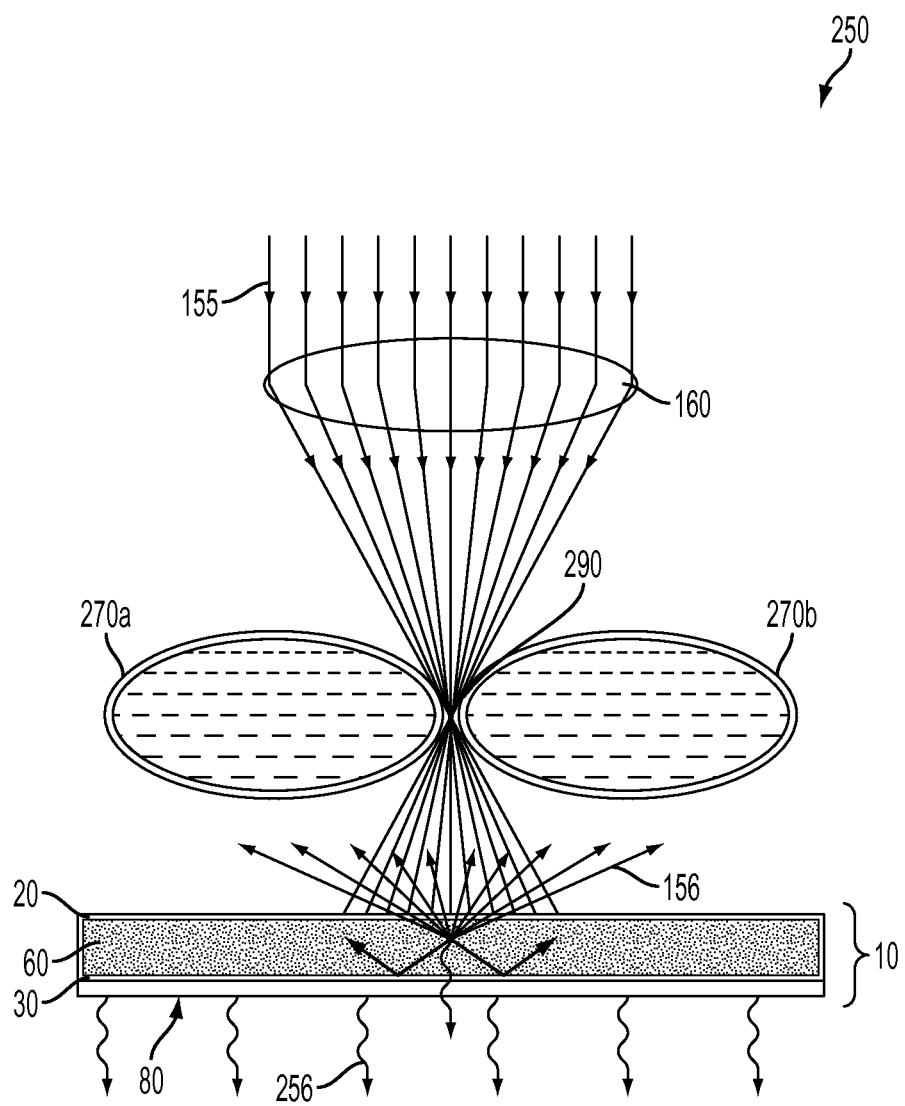
FIG. 5 is a solar-redshift module according to embodiments described herein and forming a component of the solar-redshift system of FIG. 4, highlighting structural features that repeat within the integral array.

Referring still to FIG. 5, the focusing device 160 is an optical apparatus that directs incident solar radiation along the incident-radiation optical path 155 (referring to the entire ray tracing from above the focusing device 160 until the rays enter the quantum-dot vessel 10) through the focusing gap 290 and onto the first plate 20 of the quantum-dot vessel 10. The incident solar radiation then enters the sealed cavity 60 of the quantum-dot vessel and strikes the quantum dots therein. The focusing device 160, though depicted in FIG. 5 as a converging lens, may be another appropriate optical device having an equivalent function, namely, an optical device that can direct the incident solar radiation through the focusing gap 290. Alternative devices in this regard include, for example, converging mirrors, or solar collectors such as troughs.

In FIG. 5, as a non-limiting illustrative embodiment, the focusing device 160 may be a converging lens arranged with respect to the focusing gap 290 such that the focal point of the focusing device 160, representing the narrowest width of the incident-radiation optical path 155, is located within the focusing gap 290 itself. As such, in some embodiments the width of the focusing gap 290 may be intentionally chosen as equal to, or nearly equal to, the width of the focal point of the focusing device 160. However, maintaining the position of the focal point at a fixed location within the focusing gap 290 may require additional apparatus such as single-axis tracking or dual-axis tracking, described above. Nevertheless, that the configuration shown in FIG. 5 may decrease or eliminate the need generally for dual-axis tracking, provided the focusing gap 290 is sufficiently wide to allow incident solar radiation to pass through the focusing gap 290 in all months of the year without unacceptably decreasing the intensity of light hitting the quantum-dot vessel 10.

The quantum-dot vessel 10 in the photosynthesis-enhancing solar-redshift module 250 may comprise a sealed cavity 60 defined between a first plate 20 and a second plate 30.

The first plate 20 and the second plate 30 may be hermetically sealed, as described above with reference to FIGS. 1A and 1B but not shown in FIG. 5, which depicts a continuous quantum-dot vessel shared among additional photosynthesis-enhancing solar-redshift modules not shown. In the quantum-dot vessel 10, a quantum-dot suspension is disposed within the sealed cavity 60. The quantum-dot suspension comprises quantum dots suspended in a suspension medium. The quantum dots are formed of a quantum-dot material and have a quantum-dot size, wherein the quantum dots emit a redshifted light 156 having the wavelength of increased photosynthetic response when the quantum dots are irradiated by incident solar radiation. As such, a synergy is present between the emission wavelength of the quantum dots and the wavelength of increased photosynthetic response of the living photosynthetic organism in the growth vessels 270a, 270b. Suitable quantum-dot materials, quantum-dot sizes, and suspension media, are as described above with reference to the quantum-dot vessel 10 of FIGS. 1A and 1B.

When the incident solar radiation traveling along the incident-radiation optical path 155 enters the quantum-dot vessel 10 and contacts the quantum dots therein, redshifted light 156 is emitted from the quantum dots in all directions, including downward (with respect to the orientation in FIG. 5 only) and away from the growth vessels 270a, 270b. Thus, the quantum-dot vessel 10 in each photosynthesis-enhancing solar-redshift module 250 and, referring to FIG. 4, in the integral array 201, comprises a trapping reflector 80 that reflects at least a portion of the redshifted light 156 toward the growth vessels 270a, 270b. Specifically, the trapping reflector 80 reflects the portion of redshifted light 156 that is emitted downwardly, away from the growth vessels 270a, 270b. Without the trapping reflector 80, some redshifted light 156 of the most desirable wavelengths for the energy-harvesting application involved with the photosynthesis-enhancing solar-redshift system 200 may be lost without benefiting the growth of the living photosynthetic organism.

The trapping reflector 80 can be, for example, a partly reflective coating on any surface of the second plate 30 of the quantum-dot vessel 10 or, as a further example, a reflective object contacting the surface of the second plate 30 of the quantum-dot vessel 10 opposite the growth vessels 270a, 270b so as to prevent escape of the redshifted light 156 through the second plate 30, in a direction away from the growth vessels 270a, 270b, is prevented. Additionally, the trapping reflector 80 may be reflective to the wavelength of the redshifted light 156. For example, if a wavelength of increased photosynthetic response is 680 nm (red), the trapping reflector 80 may be a layer of red paint on a surface of the second plate 30.

In some embodiments, the trapping reflector is highly transmissive of undesirable light 256 having wavelengths that are not helpful, or even harmful, to the growth of the living photosynthetic organism. The undesirable light 256 may be infrared light. The trapping reflector 80 may in some embodiments transmit 50%, in some embodiments 75%, in some embodiments 90%, or in some embodiments even 100%, of all infrared light having a wavelength of from 700 nm to 1 mm.

Because wavelengths of increased photosynthetic response generally are shorter than the 700 nm to 1 mm of infrared light, the prevalence of infrared radiation in the light emerging from the quantum-dot vessel 10 is unaffected, as compared to the prevalence of the infrared radiation in incident solar radiation. This is because the quantum dots redshift only photons having a higher energy (shorter wavelength) than the emission wavelength of the quantum dots. The emission wavelength of the quantum dots is chosen to match a wavelength of increased photosynthetic response of the living photosynthetic organism. Thus, the redshifted light in the flux emanating from the quantum-dot vessel 10 can comprise a substantial amount of unconverted infrared radiation, i.e., radiation that is not redshifted by the quantum dots because it has a longer wavelength than the emission wavelength of the quantum dots. This infrared light, if reflected toward the growth vessels 270a, 270b, may cause overheating of the living photosynthetic organism, resulting in inefficient growth of the organism, or even death of the organism. Thus, in some embodiments the trapping reflector 80 both reflects the redshifted light 156 and transmits infrared light as the undesirable light 256. Thus, in some embodiments, the photosynthesis-enhancing solar-redshift module 250 provides: (1) that the most desirable wavelengths of redshifted light 156 are produced by emission from the quantum dots; (2) that losses of redshifted light 156 due to transmission in a direction away from the growth vessels 270a, 270b are minimized or prevented entirely; and (3) that the living photosynthetic organism is isolated from most or all undesirable light 256 present in the incident solar radiation.

The photovoltaic solar-redshift modules and the photosynthesis-enhancing solar-redshift modules have been described above as components of solar-redshift systems and as non-limiting examples of solar-redshift modules having a gap-to-reflector configuration or a gap-to-vessel configuration. In additional embodiments, solar-redshift modules having a parallel-plate configuration will now be described with reference to the exemplary embodiments of a parallel-plate solar redshift system of FIGS. 6-11. Just as the solar-redshift systems having modules with a gap-to-reflector configuration or a gap-to-vessel configuration may be adaptable, the parallel-plate solar-redshift systems may be adapted to include photovoltaic materials, photosynthetic organisms in growth vessels, or both, as collecting targets for capturing energy from light sources such as incident solar radiation.

Figure 6:
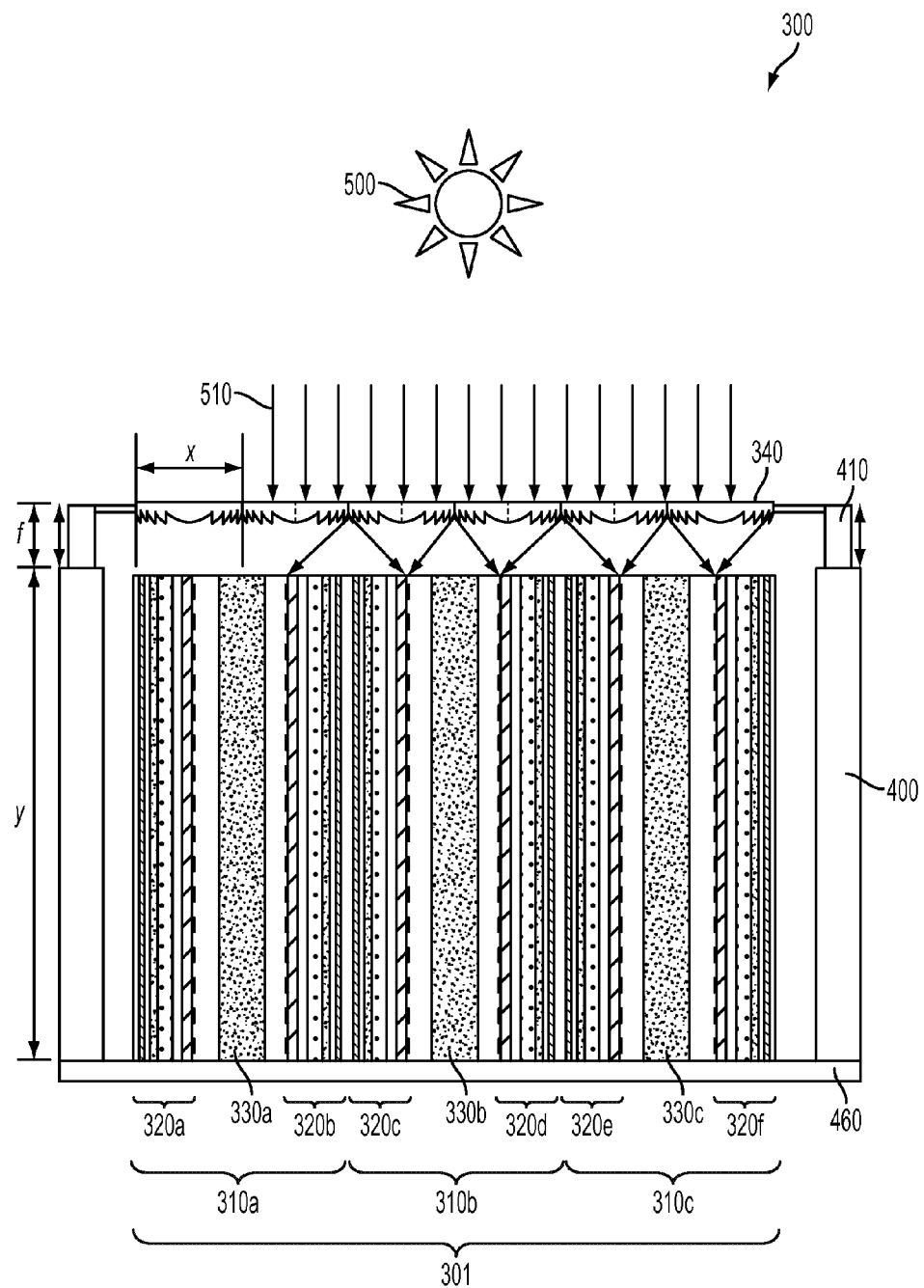
FIG. 6 is a schematic plan view of a solar-redshift system according to embodiments described herein, which has a parallel-plate configuration.

Referring to the illustrative embodiment of FIG. 6, a parallel-plate solar-redshift system 300 may include a parallel-plate configuration 301 of solar-redshift modules 310a, 310b, 310c and at least one focusing device 340. It should be understood foremost that the parallel-plate solar-redshift system 300 of FIG. 6 is shown as containing three solar-redshift modules 310a, 310b, 310c for clarity purposes only. In practice, however, the parallel-plate solar-redshift system according to the embodiments to be described below may contain any desired number of solar-redshift modules such as 1, 2, 5, 10, 50, 100, 500, 1000, 10,000, or even more than 10,000, for example.

As used in the context of the parallel-plate solar-redshift system 300, the term "parallel-plate configuration" means that the functional components of the parallel-plate solar-redshift system 300 are configured as a series of parallel plates, wherein parallel plates of individual solar-redshift modules are, as a group, parallel to other parallel plates of neighboring solar-redshift modules. As used herein with regard to parallel plates, generally the term "plate" means a three-dimensional structure having one dimension substantially smaller than at least one of the other two dimensions, in some embodiments of both of the other two dimensions. With regard to the dimensions of any one parallel plate, as used herein, the "length" of a plate refers to the dimension measured from the edge of the plate that faces the focusing device 340 during operation of the parallel-plate solar-redshift system 300 to the edge of the plate opposite the focusing device 340; the "width" or the "thickness" of a plate is measured perpendicular to the length of the plate, from an edge of the plate that faces a neighboring plate to an opposite edge of the plate that faces another neighboring plate.

In the parallel-plate solar-redshift system 300 of FIG. 6, for example, the width of the parallel plates in the direction of the dimension labeled x may be substantially smaller than the length in the direction of the dimension labeled y, and also may be substantially smaller than a depth into the plane of the figure but not apparent from the figure itself. In some non-limiting embodiments, the plates may be rectangular solids or may be rectangular solids with cavities defined therein. Regardless, it should be understood that the plates need not be rectangular solids and need only be amenable to arrangement in a parallel-plate configuration. In some embodiments, however, the assembly width x is optimized with respect to the plate length y. In some embodiments, the ratio y/x of the plate length y to the assembly width x may be chosen such that y/x is from about 5:1 to about 20:1, such as from about 5:1 to about 15:1, from about 8:1 to about 12:1, or about 10:1. In this context, "about" may be regarded as encompassing a range of ±10% from a stated figure (e.g., "about 10:1" may be regarded as from 9:1 to 11:1).

An optimal ratio y/x may result in a desirable intensity of redshifted light being directed to the collecting targets 330a, 330b, 330c along their entire respective lengths. As used here, the term "desirable intensity" means an intensity that is less than the full intensity of the sun and is conducive to the chosen energy harnessing application for which the parallel-plate solar redshift system 300 is used. For example, certain types of photosynthetic organisms may thrive under a maximum intensity of redshifted light that is approximately 10% the intensity of full sun. By appropriate selection of x and y, a desirable intensity can be achieved. In some embodiments, the substantially uniform intensity is sufficient for producing energy from the entire length of the collecting targets 330a, 330b, 330c, whether the collecting targets 330a, 330b, 330c are photovoltaic plates or growth vessels containing living photosynthetic organisms.

Each of the solar-redshift modules 310a, 310b, 310c in the parallel-plate solar-redshift system 300 may include at least one solar-radiation conversion assembly 320a, 320b, 320c, 320d, 320e, 320f and a collecting target 330a, 330b, 330c. In the embodiment of FIG. 6, each solar-redshift module 310a, 310b, 310c includes two opposing solar-radiation conversion assemblies. For example, solar-redshift module 310a contains a first solar-radiation conversion assembly 320a and a second solar-radiation conversion assembly 320b opposing the first solar-radiation conversion assembly 320a, such that the two solar-radiation conversion assemblies 320a, 320b surround a single collecting target 330a. Even so, it should be understood that the solar-redshift module 310a may still function even in the absence of either the first solar-radiation conversion assembly 320a or the second solar-radiation conversion assembly 320b.

Reference now will be made to FIGS. 6-10 to describe the collecting target 330a and the various components of the solar-radiation conversion assemblies 320a, 320b, all of which being themselves components of the solar-redshift module 310a. It should be understood that the description of solar-radiation conversion assemblies 320a, 320b applies equally to the solar-radiation conversion assemblies in other solar-redshift modules of the parallel-plate solar-redshift system 300.

Figure 7:
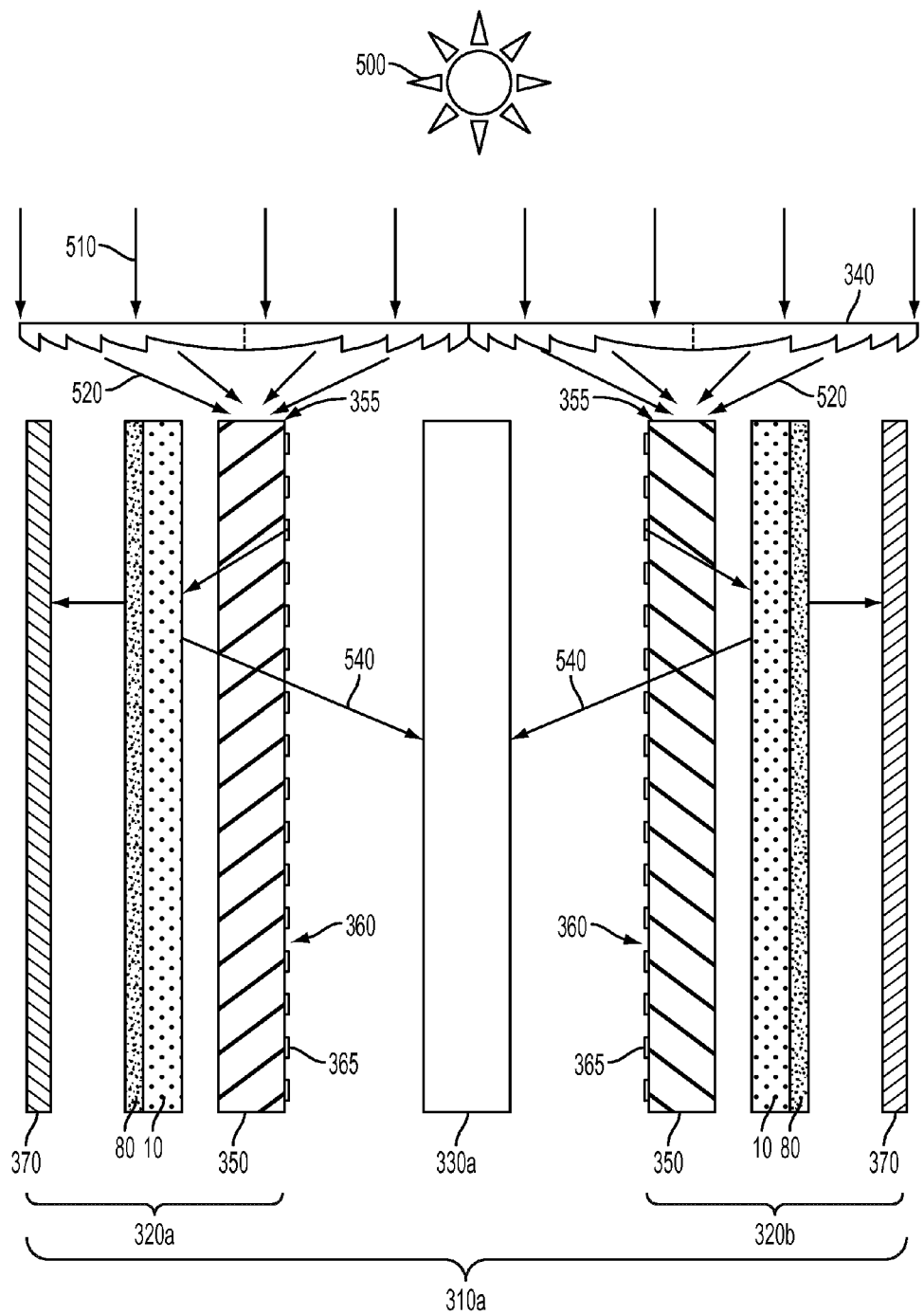
FIG. 7 is an exploded plan view of the solar-redshift system of FIG. 6.

Referring particularly to FIG. 7, the solar-redshift module 310a includes a collecting target 330a and solar-radiation conversion assemblies 320a, 320b. It should be understood that FIG. 7 is presented as an exploded view and that each of the parallel plates that form the collecting target 330a and the components of the solar-radiation conversion assemblies 320a, 320b may be touching or may have some amount of distance between them. In some embodiments, each of the parallel plates may contact neighboring plates. In other embodiments, some parallel plates have space between them. In still other embodiments, some parallel plates touch and others do not. In embodiments where at least some of the parallel plates do not touch neighboring plates, thermal management of the parallel-plate solar-redshift system 300 as a whole may outweigh the space-saving benefit of having all parallel plates touch. It should be recognized that FIGS. 6-10 are intended to be regarded as schematic illustrations only. Therefore, except as stated otherwise herein, FIGS. 6-10 are not intended to limit embodiments of the parallel-plate solar-redshift system 300 to any particular absolute thicknesses of the parallel plates in the dimension parallel to the assembly width x in FIG. 6, or to any relative thickness of any one of the parallel plates to any other parallel plate. Though illustrative embodiments are provided herein of exemplary thicknesses and relative thicknesses, it should be understood that such thicknesses and relative thicknesses may be optimized according to the desired application, as well as to the choices of quantum dots and collecting targets.

In some embodiments, the collecting target 330a may be a growth vessel containing a living photosynthetic organism. The growth vessel may contain a growth medium for sustaining the living photosynthetic organism. The living photosynthetic organism may have a wavelength of increased photosynthetic response. In such embodiments, the growth vessel may be any enclosed container that can be incorporated in the parallel-plate configuration. The growth vessel may be made of any material suitable for growing a photosynthetic organism therein such as, for example glass or acrylic. The living photosynthetic organism and the growth medium may be any of the photosynthetic organisms or growth media described above with reference to the embodiments of photosynthesis-enhancing solar-redshift systems 200 (FIG. 4). In this regard, the concept of the wavelength of increased photosynthetic response has also been fully described above with regard to the photosynthesis-enhancing solar-redshift systems 200 and applies equally to the parallel-plate solar-redshift system 300. Though in non-limiting illustrative embodiments, in the parallel-plate solar redshift system 300, the growth vessels may have thicknesses of from about 1 mm to about 10 mm, the thickness of the growth vessels may be less than 1 mm or greater than 10 mm, depending on the application. The limit in thickness of a growth vessel in a parallel-plate configuration such as in the parallel-plate solar redshift system 300 may be limited to the extent that living photosynthetic organisms (e.g., algae) in the center of the growth vessel may be shaded by other organisms closer to the sides of the growth vessel closest to illumination sources. Also, the shading effect may be overcome to some extent by turbulent flow within the growth vessel.

In other embodiments, the collecting target 330a may be a photovoltaic plate comprising a photovoltaic material having a wavelength of increased sensitivity. The photovoltaic plate may be formed from the photovoltaic material or may be formed from a suitable substrate such as a metal, silicon, ceramic, or plastic, for example, which is coated with the photovoltaic material or otherwise has a layer of photovoltaic material disposed thereon. A layer of photovoltaic material disposed on the photovoltaic plate may be a continuous layer or may be a layer patterned in a suitable manner that enables electrical energy to be efficiently harvested from the photovoltaic plate. The photovoltaic material may be any of the photovoltaic materials described above with reference to the embodiments of photovoltaic solar-redshift systems 100 (FIG. 2). In this regard, the concept of the wavelength of increased sensitivity has also been fully described above with regard to the photovoltaic solar-redshift systems 100 and applies equally to the parallel-plate solar-redshift system 300. The photovoltaic plate may additionally include electrical connections (not shown) adapted to utilize electrical energy produced by the photovoltaic plate during the operation of the parallel-plate solar-redshift system 300.

With regard to the parallel-plate solar-redshift system 300 (FIG. 6) as a whole, in some embodiments either each of the collecting targets 330a, 330b, 330c is a growth vessel or each of the collecting targets 330a, 330b, 330c is a photovoltaic plate. In other embodiments of the parallel-plate solar-redshift system 300, some of the collecting targets (330a and 330c, for example) may be growth vessels, while others (330b, for example) may be photovoltaic plates.

Referring to FIG. 7, in the solar-redshift module 310a, the at least one solar-radiation conversion assembly 320a (and/or 320b) includes a waveguide 350, an infrared-radiation absorber 370, and a quantum-dot vessel 10 interposed between the waveguide 350 and the infrared-radiation absorber 370.

The quantum-dot vessel 10 has been described in detail above with regard to embodiments of both the photovoltaic solar-redshift systems 100 (FIG. 2) and the photosynthesis-enhancing solar redshift systems 200 (FIG. 3). In the parallel-plate solar-redshift systems 300, the quantum-dot vessel 10 is configured as a plate adapted to fit into the parallel-plate configuration. The quantum-dot vessel 10 may include a sealed cavity that contains a quantum-dot suspension including quantum dots. Though not apparent in FIG. 7, the quantum-dot vessel 10 may include the features of the quantum-dot vessel 10 in FIG. 1B such as the sealed cavity 60 defined between a first plate 20 and a second plate 30 and, optionally, a sealing edge 40 and separator structures 50. may be defined between first and second plates The quantum dots are chosen such that they emit redshifted light having the target wavelength of the collecting target 330a (e.g., the wavelength of increased photosynthetic response or the wavelength of increased sensitivity, as appropriate to the conversion target with which the quantum-dot vessel 10 is associated) when irradiated by incident solar radiation. These concepts with regard to the parallel-plate solar-redshift systems 300 are identical to the respective concepts as they pertain to the photovoltaic solar-redshift systems 100 (FIG. 2) and the photosynthesis-enhancing solar redshift systems 200 (FIG. 3).

The quantum-dot vessel 10 may further include a trapping reflector 80 that reflects the redshifted light toward the collecting target 330a but transmits all, or at least a portion of, the infrared light from the incident solar radiation in a direction away from the collecting target 330a. Specifically, the trapping reflector 80 may reflect the portion of redshifted light that is emitted in a direction away from the collecting target 330a. Without the trapping reflector 80 some redshifted light of the most desirable wavelengths for the energy-harvesting application involved with the parallel-plate solar-redshift system 300 may be lost without benefiting the system. In some embodiments, the trapping reflector may be a coating layer on a surface of the quantum-dot vessel 10 farthest from the collecting target 330*a*. For example, the coating layer may be a paint having the desired reflectivity and transmissivity characteristics. In some embodiments, the trapping reflector 80 may be reflective to the wavelength of the redshifted light yet transmissive of other wavelengths of light. Thus, the trapping reflector 80 may ensure not only that the most desirable wavelengths of redshifted light produced by emission from the quantum dots in the quantum-dot vessel 10 are effectively utilized, but also that losses of redshifted light due to reflection away from the collecting target 330*a* are minimized or prevented entirely.

In non-limiting illustrative embodiments, the quantum-dot vessel 10 may have a thickness of from about 300 μm to about 1.5 mm. The thickness may include, for example, the thickness of two sheets of encapsulating material such as glass (for example, a first plate 20 and a second plate 30, see FIG. 1B) that enclose a sealed cavity 60 (FIG. 1B) containing a suspension of quantum dots. Thus, in the illustrative embodiments the sheets of encapsulating material each may be from about 100 μm to about 700 μm thick and the sealed cavity that contains the quantum dots may be about 100 μm thick. It should be understood that the illustrative thicknesses of growth vessel are not meant to be limiting and that the growth vessels may have thicknesses less than 300 μm or substantially greater than 1.5 mm. As noted above, the thicknesses of the quantum-dot vessel 10 are shown schematically and not to scale in FIGS. 6-10.

Referring again to FIG. 7, the infrared-radiation absorber 370 of the at least one solar-radiation conversion assembly 320*a* (and/or 320*b*) may be any material that absorbs infrared radiation, typically by converting it to heat. In some embodiments, the infrared-radiation absorber 370 is physically isolated from the quantum-dot vessel 10 or any other neighboring parallel plate to enable removal of the heat. Such heat may be efficiently removed in some embodiments by simply allowing air to circulate through the space between the infrared-radiation absorber 370 and the neighboring parallel plate. In other embodiments, additional structures may be contemplated for insertion between the infrared-radiation absorber 370 and neighboring parallel plates, such as a coolant plate (not shown) or cooling loop (not shown) through which a coolant medium such as water may be circulated. In some embodiments, each solar-radiation conversion assembly 320*a*, 320*b* has one unique infrared-radiation absorber 370 not shared by any neighboring solar-radiation conversion assembly. In other embodiments not shown, solar-radiation conversion assemblies of neighboring solar-redshift modules may share a common infrared-radiation absorber 370.

In some embodiments, the infrared-radiation absorber 370 of the at least one solar-radiation conversion assembly 320*a* (and/or 320*b*) may be a photovoltaic plate comprising a photovolatic material such as those described above for use as the collecting target 330*a*, particularly those capable of converting infrared light to electrical energy. In such embodiments, the infrared-radiation absorber 370 may be a photovoltaic plate, even if the collecting target 330*a* is a growth vessel. Thus, energy-collecting benefits may be realized through not only the collecting target 330*a*, but also the infrared-radiation absorber 370, particularly from the infrared radiation that may have been converted to heat.

Generally, the thickness of the infrared-radiation absorber 370 may vary to the application of the parallel-plate solar redshift system 300. In some embodiments, it may be advantageous if the infrared-radiation absorber 370 is sufficiently thick (for example, 1 cm to 10 cm) to absorb a substantial amount of heat during daylight hours and then radiate the heat during cooler nighttime hours. The ability of the infrared-radiation absorber 370 to absorb and radiate heat in this manner may advantageously maintain consistency of the temperature of the collecting target 330*a*, particularly when the collecting target 330*a* is a growth vessel containing a living photosynthetic organism (e.g., algae) that grows optimally at a particular range of temperatures.

The at least one solar-radiation conversion assembly 320*a* (and/or 320*b*) is arranged in the parallel-plate configuration such that the waveguide 350 of the at least one solar-radiation conversion assembly 320*a* (and/or 320*b*) is interposed between the quantum-dot vessel 10 of the at least one solar-radiation conversion assembly 320*a* (and/or 320*b*) and the collecting target 330*a*.

According to some embodiments, the waveguide 350 of the at least one solar-radiation conversion assembly 320*a* (and/or 320*b*) may be a transparent or translucent material through which focused solar radiation 520 can travel by total internal reflection after entering through a sun-facing edge 355 of the waveguide 350. Suitable materials for the waveguide 350 in this regard include, without limitation, glasses and substantially clear polymers such as acrylics, for example. In some embodiments, the waveguide 350 may be transparent to essentially all wavelengths of the solar spectrum. In other embodiments, the waveguide 350 may be colored, such as by an appropriate dye, such that the waveguide 350 is transparent to some wavelengths but absorbs other wavelengths. Generally, though in some embodiments it may be desirable that the waveguide 350 be transparent over a broad range, such as the entire solar spectrum, in some embodiments the transparency of the waveguide 350 over wavelengths shorter than the target wavelength (i.e., the wavelength of increased sensitivity and/or the wavelength of increased photosynthetic response) such as, for example, wavelengths shorter than about 700 nm, that can be redshifted by the quantum dots in the quantum-dot vessel 10.

Figure 8:
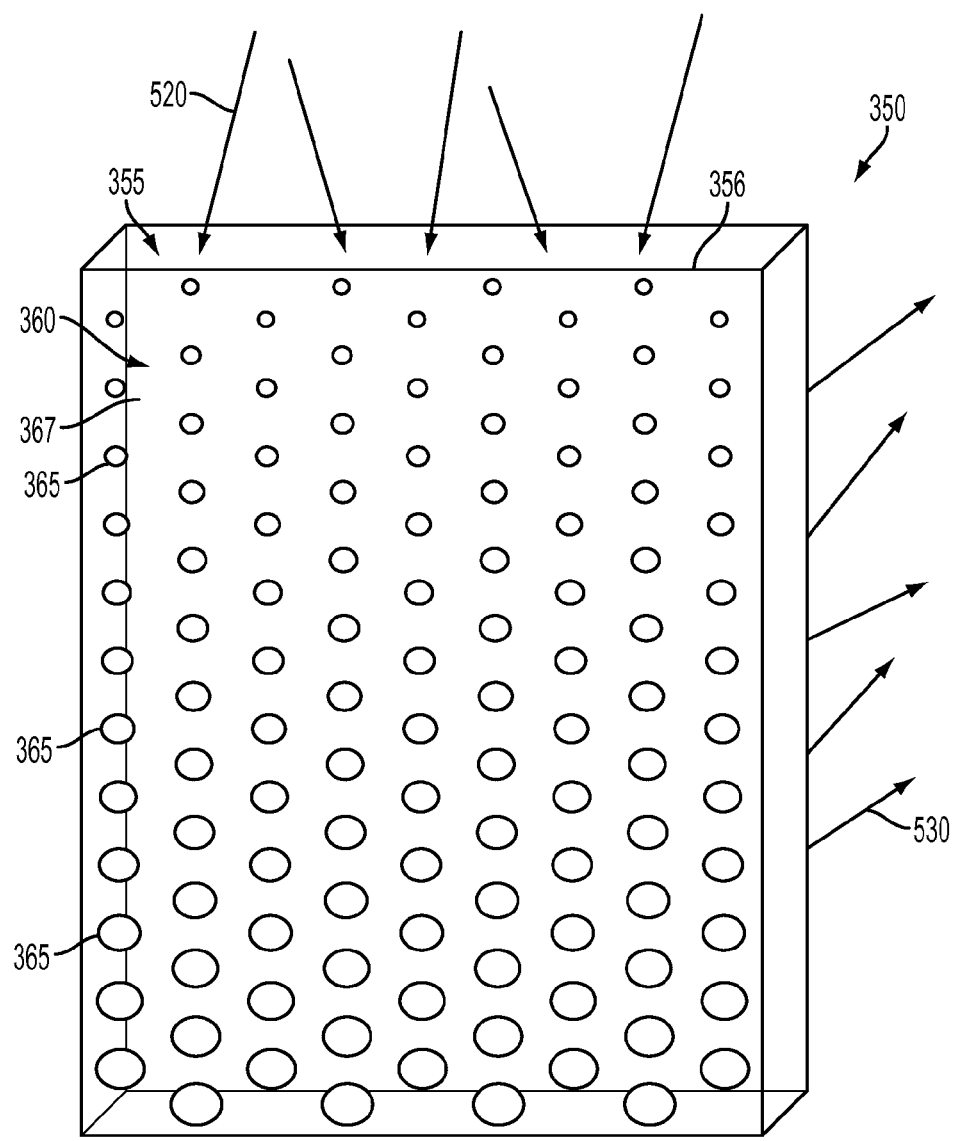
FIG. 8 is a perspective view of a waveguide according to embodiments described herein, a component of parallel-plate solar-redshift systems such as the solar-redshift system of FIG. 6.
Figure 9:
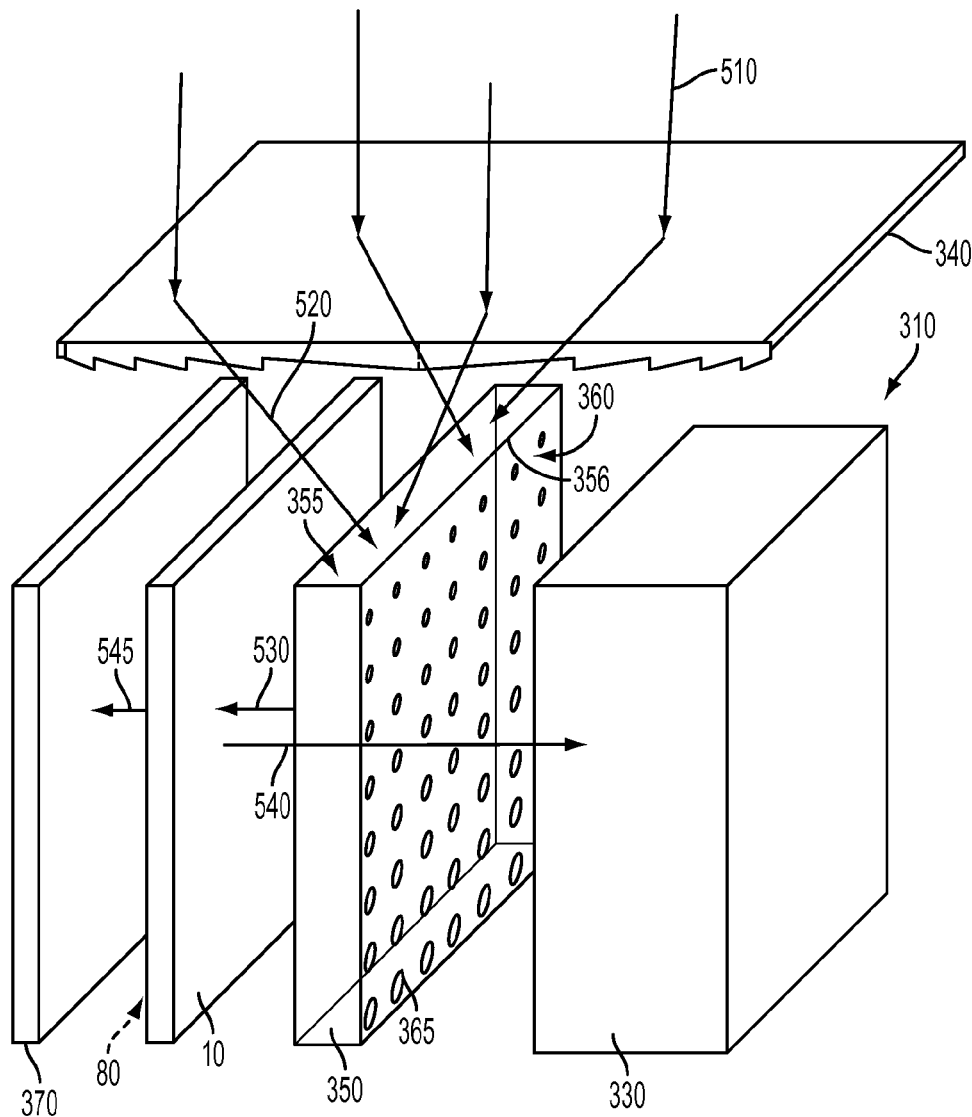
FIG. 9 is an exploded perspective view of a solar-redshift module according to embodiments described herein, a component of the solar-redshift system of FIG. 6.
Figure 10:
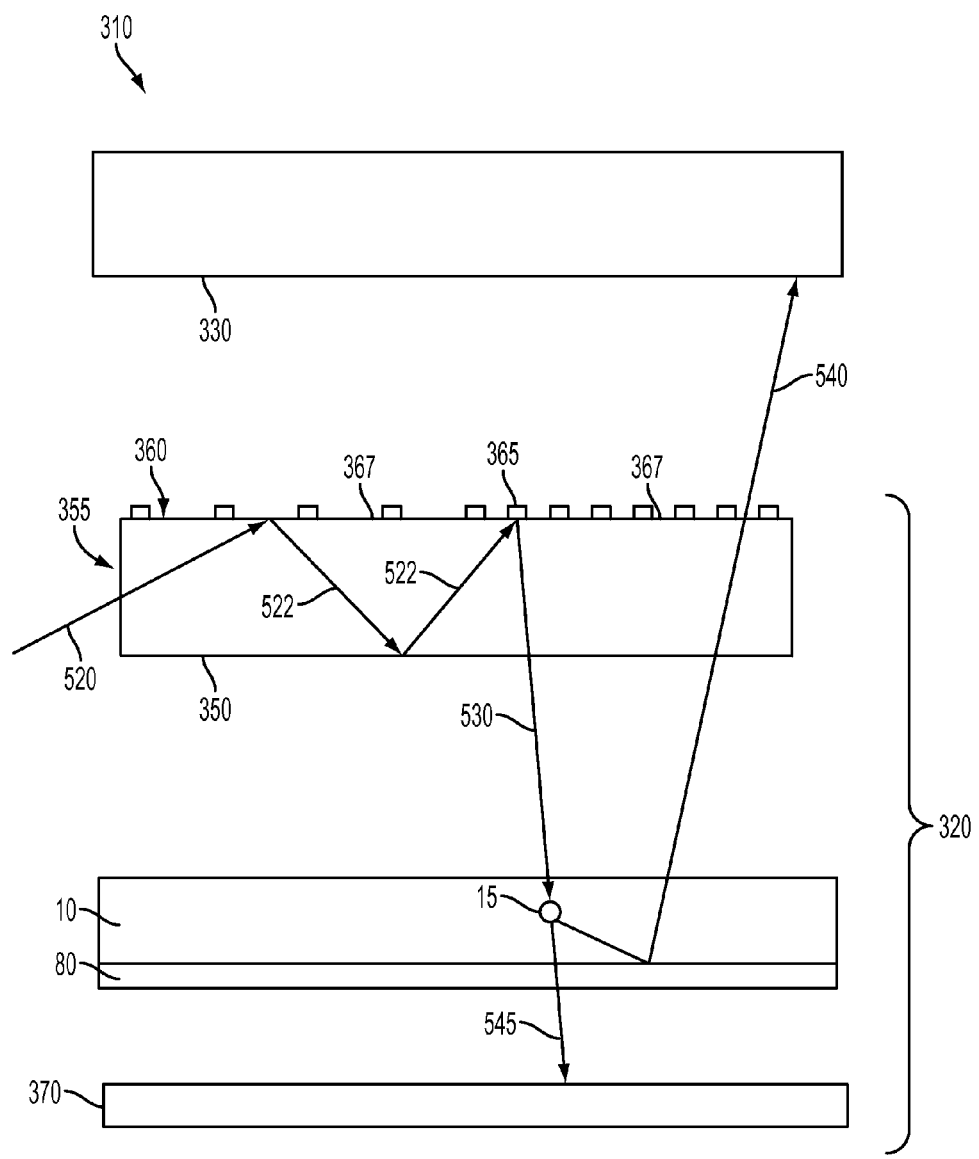
FIG. 10 is a schematic diagram illustrating an example of a pathway of a light ray emanating from incident solar radiation and travelling through various components of the solar-redshift system of FIG. 6.

Additional features of the waveguide 350 will be described now with reference to FIGS. 8-10. It should be understood that the rectangular shapes of the waveguide 350 of FIGS. 8-10 are presented as illustrative embodiments only and that neither the shape nor the proportions of the waveguide 350 should be regarded as limiting. As shown in the illustrative embodiment of FIG. 8, the waveguide 350 includes a frustrating surface 360. The frustrating surface 360 may include an unblocked portion 367 and may further include scattering features 365 dispersed across the frustrating surface 360.

The schematic depictions of FIGS. 9 and 10 clarify the functionality of the frustrating surface 360 and of the waveguide 350 as a component of the solar-redshift module 310. In general, the frustrating surface 360 scatters any guided solar radiation 522 (FIG. 10) within the waveguide 350 toward the quantum-dot vessel 10 and permits redshifted light 540 to pass through the waveguide 350 from the quantum-dot vessel 10 toward the collecting target 330. During operation of the parallel-plate solar-redshift system 300, as will be described in greater detail below, incident solar radiation 510 is focused by the at least one focusing device 340. The resulting focused solar radiation 520 is directed into the waveguide 350 through a sun-facing edge 355 of the waveguide 350.

One light ray of the solar radiation inside the waveguide 350 is shown in FIG. 10 as guided solar radiation 522. It should be understood that the guided solar radiation 522 travels through the waveguide 350 at various angles, depending on the angle at which the focused solar radiation 520 enters through the sun-facing edge 355. At least a portion of the guided solar radiation 522 may be trapped in the waveguide 350 by total internal reflection, but eventually the guided solar radiation 522 will strike a scattering feature 365 of the frustrating surface 360, wherein the guided solar radiation 522 would not be reflected by total internal reflection. For this purpose, scattering features 365 may be provided on the frustrating surface 360 to scatter the guided solar radiation 522 generally toward the quantum-dot vessel 10. Though for sake of clarity only one ray of scattered solar radiation 530 is shown in FIG. 10, it should be understood that the guided solar radiation 522 striking the scattering features 365 may be scattered in many directions, generally toward the quantum-dot vessel 10.

An non-limiting illustrative embodiment of a configuration of the frustrating surface 360 of the waveguide 350 is shown in FIG. 8. In the exemplary configuration of FIG. 8, the scattering features 365 are arranged as a pattern of dots having increasing size with respect to distance from the sun-facing edge 355 of the waveguide 350. Nevertheless, even at the lowest region of the frustrating surface 360 (i.e., farthest from the sun-facing edge 355), the frustrating surface 360 includes unblocked portion 367 between the scattering features 365.

In some embodiments, the scattering features 365 may be any structure and/or marking that frustrates total internal reflection within the waveguide 350 itself. For example, the scattering features 365 may be a coating material such as an opaque paint or may be an etched portion of the frustrating surface 360. If the scattering features 365 are paint dots, for example, in one illustrative embodiment the paint dots may be formed from a white paint that does not inherently absorb any portion of guided solar radiation 522 that strikes the paint dots from inside the waveguide 350. Increasing the size of the scattering features 365 with respect to distance from the sun-facing edge 355 may cause the intensity of scattered solar radiation 530 emerging out the back side of the waveguide 350 (parallel to and opposite the frustrating surface 360) to be substantially uniform across the entire surface area of the back side of the waveguide 350. The uniform intensity may result because the guided solar radiation 522 may have a higher intensity nearest the sun-facing edge 355 of the waveguide 350, such that scattering features 365 that are smaller, fewer in number, or both, may cause an equivalent intensity of scattered solar radiation 530 as the scattering features 365 far from the sun-facing edge 355 that are larger, more numerous, or both. In this regard, the configuration of scattering features 365 of FIG. 8 may have any configuration known to be useful for the purpose of providing uniform light output across a surface area such as in liquid-crystal display (LCD) backlight technologies, for example.

Referring to FIGS. 8-10, when the scattered solar radiation 530 reaches the quantum-dot vessel 10, which contains a quantum-dot suspension, it encounters quantum dots, as particularly illustrated in FIG. 10 quantum dot 15. As described above, the quantum dot 15 has an emission wavelength unique to the material of the quantum dot 15 and the size of the quantum dot 15, wherein photons having a higher energy (shorter wavelength) than the emission wavelength may be absorbed by the quantum dot and subsequently re-emitted as a photon of the emission wavelength. The quantum dot 15 does not absorb photons having a lower energy (longer wavelength) than the emission wavelength of the quantum dot 15. Thus, if the scattered solar radiation 530 has a higher energy (shorter wavelength) than the emission wavelength of the quantum dot 15, the quantum dot 15 absorbs the scattered solar radiation 530 and emits redshifted light 540 having the emission wavelength. Conversely, if the scattered solar radiation 530 has a lower energy (longer wavelength) than the emission wavelength of the quantum dot 15, the quantum dot 15 does not absorb or redshift the scattered solar radiation 530.

As described above, the quantum-dot vessel 10 includes a trapping reflector 80 that, in some embodiments, is reflective to desirable wavelengths such as those of the redshifted light 540 and is transmissive of undesirable wavelengths such as infrared, for example. This is illustrated in FIG. 10, in which undesirable light 545, which may or may not encounter the quantum dot 15 but by no means is absorbed by the quantum dot, passes through the trapping reflector 80 and is allowed to pass toward the infrared-radiation absorber 370. At the infrared-radiation absorber 370 the undesirable light 545 is absorbed, and/or converted to heat, and/or otherwise removed from the parallel-plate solar-redshift system 300. On the other hand, the redshifted light 540 is reflected back toward the waveguide 350, passes through the waveguide 350, and emerges through the frustrating surface 360 of the waveguide 350 in the unblocked portion 367 between the scattering features 365.

The redshifted light 540 that emerges from the frustrating surface 360 of the waveguide 350 proceeds to reach the collecting target 330, where it may be used to enhance efficiency of energy production. For example, in some embodiments the redshifted light 540 may enhance growth of the living photosynthetic organism when the collecting target 330 is a growth vessel and the living photosynthetic organism has a wavelength of increased photosynthetic response near or equal to the wavelength of the redshifted light 540. In other embodiments the redshifted light 540 may cause the photovoltaic material to produce energy at increased efficiency when the collecting target 330 is a photovoltaic plate and the photovoltaic material has a wavelength of increased sensitivity near or equal to the wavelength of the redshifted light 540.

Having described above the components and general principles that relate to the solar-redshift modules 310*a*, 310*b*, 310*c* of the parallel-plate solar-redshift system 300, the interaction of the solar-redshift modules 310*a*, 310*b*, 310*c* with the at least one focusing device 340 and the application of the parallel-plate solar-redshift system 300 for energy harnessing now will be described with reference to FIGS. 6, 7, 11A, and 11B.

In the parallel-plate solar-redshift system 300, the at least one focusing device 340 focuses the incident solar radiation 510 (such as radiation emanating directly from the sun 500, for example) onto sun-facing edges 355 of the waveguides 350 of the solar-radiation conversion assemblies 320*a*, 320*b* in respective solar-redshift modules 310*a*. In the illustrative embodiments of FIGS. 6 and 7, the at least one focusing device 340 is a fresnel lens having multiple zones, each of which focuses the incident solar radiation 510 onto a sun-facing edge 355 of one respective waveguide 350. In some orientations of the parallel-plate solar-redshift system 300 of FIG. 6 and the solar-redshift module 310*a* of FIG. 7 during their operation, the sun 500 in FIGS. 6 and 7 moves into or out of the planes of the respective figures during the course of a day, not across the respective figures from left to right. It should be understood that the at least one focusing device 340 need not be such a fresnel lens and that any suitable apparatus may be used such as an array of converging lenses, for example. In some embodiments, however, substantially all of the incident solar radiation 510 can be focused onto the sun-facing edges 355 of the waveguides 350, effectively leaving in a shadow the sun-facing edges of other plates such as the collecting targets 330a, 330b, 330c and the quantum dot vessels 10.

In some embodiments, the at least one focusing device 340 may be mounted on an outer housing 400 of the parallel-plate solar-redshift system 300. The focusing device may be substantially parallel to a base support 460 into which the parallel plates may be fastened. The outer housing 400 may additionally include an azimuthal focus adjustment mechanism 410 (shown schematically in FIG. 6) that moves the at least one focusing device 340 toward or away from the parallel plates. Particularly in the illustrative embodiment of FIG. 6, the azimuthal focus adjustment mechanism 410 may change the focal distance f of the at least one focusing device 340 to optimize the amount of incident solar radiation 510 that is focused directly onto the sun-facing edges 355 of the waveguides 350. In some embodiments, the sun-facing edges 355 of the waveguides 350 are oriented such that a lateral edges 356 (FIGS. 8 and 9) of the waveguides 350 run from east to west. Thus, during operation of the parallel-plate solar-redshift system 300, as the sun 500 moves through the sky from east to west during the course of one day, the azimuthal focus adjustment mechanism 410 may be used to maintain the focus of the incident solar radiation 510 on the sun-facing edges 355 of the waveguides 350 by simply changing the focal distance f. In this regard, the azimuthal focus adjustment mechanism 410 in combination with the at least one focusing device 340 according to embodiments herein may be a configuration that alleviates a need for a more complicated system of solar tracking over the course of a day. Without the azimuthal focus adjustment mechanism 410, for example, solar tracking over the course of a day may require mechanisms and apparatus that rotate and/or tilt the entire parallel-plate configuration of the parallel-plate solar-redshift system 300.

Figure 11A:
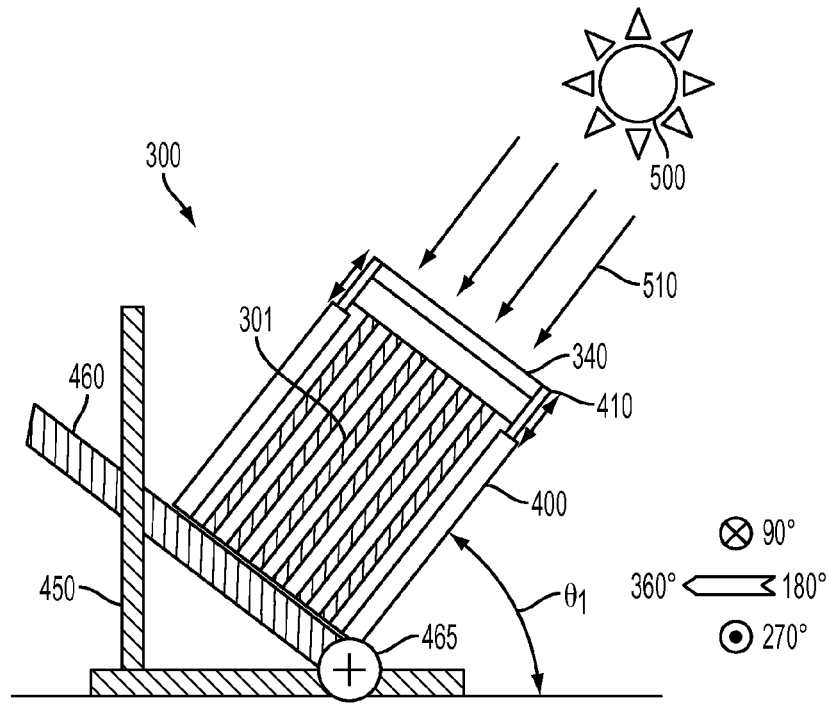
FIG. 11A is a schematic side-view of a solar-redshift system according to embodiments described herein, wherein the solar-redshift system is disposed on a platform for elevational adjustment of the solar-redshift system during the course of a calendar year and is inclined to an exemplary summer-solstice position.
Figure 11B:
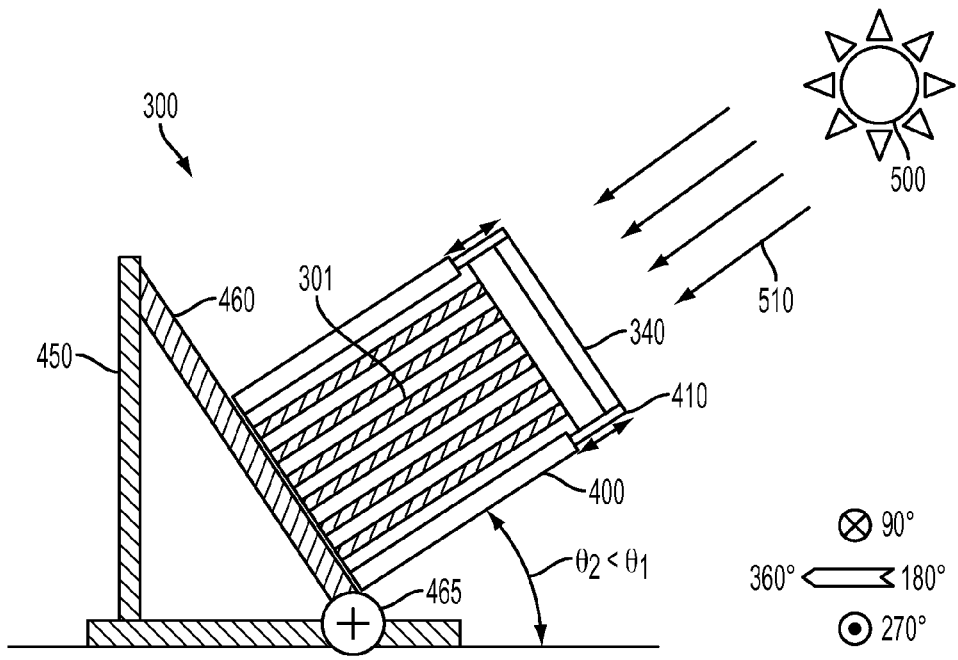
FIG. 11B is the solar-redshift system and platform of FIG. 11A, elevationally adjusted to a lower position than the summer-solstice position of FIG. 11A, as may be appropriate at the winter solstice, for example.

The parallel-plate solar-redshift system 300 is shown in FIGS. 11A and 11B schematically in operational positions on a support structure 450. It should be understood that the configuration of FIGS. 11A and 11B together represents only one simplified example of how the parallel-plate solar-redshift system 300 may be implemented and that numerous other configurations are possible. In the illustrative embodiment, the parallel-plate solar-redshift system 300 may rest on a base support 460 that is part of the support structure 450. The base support 460 may be inclined with respect to the ground and may be operatively connected to any suitable elevational adjustment mechanism (not shown) that adjusts the inclination of the base support 460. For example, adjustment of the inclination of the base support 460 may include movement of the base support 460 about a pivot point 465.

In the schematic depiction of FIG. 11A, the base support 460 is set to provide a summer-solstice inclination angle $\theta_1$ to the outer housing 400. In FIG. 11B, the base support 460 is set to provide a winter-solstice inclination angle $\theta_2$ to the outer housing 400. Because the track of the sun across the sky daily from east to west occurs at a lower elevation in the winter than in the summer, naturally the summer-solstice inclination angle $\theta_1$ is less than the winter-solstice inclination angle $\theta_2$. For purposes of illustration only, the sun 500 in FIG. 11A is shown at solar noon on the summer solstice, and the sun 500 in FIG. 11B is shown at solar noon on the winter solstice. As used herein, the term "solar noon" refers to the time of a given day when the sun reaches its highest elevation in the sky over where the parallel-plate solar-redshift system 300 is being operated, without regard to the local time established at the same location by arbitrary time-zone boundaries.

The parallel-plate solar-redshift system 300 of FIGS. 11A and 11B is oriented in an exemplary manner for how it may be used in the northern hemisphere, particularly north of the Tropic of Cancer. Namely, both the summer-solstice inclination angle $\theta_1$ and the winter-solstice inclination angle $\theta_2$ are expressed as elevation angles, for which an elevation of 0° would cause the side of the focusing device 340 facing the sun 500 to face due south (shown as bearing 180°) and an elevation of 90° would cause the side of the focusing device 340 facing the sun 500 to face straight up (i.e., toward the zenith). Due east (indicated as bearing 90°) is depicted into the plane of FIGS. 11A and 11B, and due west (indicated as bearing 270°) is depicted out of the plane of FIGS. 11A and 11B. Accordingly, the parallel-plate configuration 301 is oriented such that the lateral edges 356 of the sun-facing edges 355 of the waveguides (see FIG. 9, for example) run from east to west.

In general, if the parallel-plate solar-redshift system 300 is deployed at a latitude L north of the Tropic of Cancer as provided in FIGS. 11A and 11B, the summer-solstice inclination angle $\theta_1$ may be expressed according to the equation $\theta_1 \approx 90° - (L - 23.5°)$ and the winter-solstice inclination angle $\theta_2$ may be expressed according to the equation $\theta_2 \approx 90°(L + 23.5°)$. These relationships hold for locations south of the Tropic of Capricorn, provided the parallel-plate solar-redshift system 300 is oriented in reverse, such that an elevation of 0° would cause the side of the focusing device 340 facing the sun 500 to face due north (shown as bearing 360°) instead of due south.

North of the Tropic of Cancer and south of the Tropic of Capricorn, when the parallel-plate solar-redshift system 300 is operated over the course of the year, the elevation angle of the base support 460 may be adjusted to match the elevation of the sun 500 on a given day. It should be understood that the elevation of the sun 500 on a given day is readily ascertainable from common sources such as astronomical tables, for example. In some embodiments, the elevation angle of the base support 460 may be decreased incrementally from the summer-solstice inclination angle $\theta_1$ at the summer solstice to the winter-solstice inclination angle $\theta_2$ at the winter solstice then increased incrementally from the winter-solstice inclination angle $\theta_2$ to the summer-solstice inclination angle $\theta_2$ at the next summer solstice. The incremental adjustments of inclination angle may be made in a manner that causes incident solar radiation 510 to strike the focusing device 340 substantially perpendicularly at solar noon each day over the course of an entire year.

Though not illustrated in FIGS. 11A and 11B, it should be apparent that if the parallel-plate solar-redshift system 300 is deployed between the Tropic of Cancer and the Tropic of Capricorn, on two days of the year (i.e., when the sun 500 is directly overhead), the inclination angle of the base support 460 may be 90°. Then, while the sun 500 is directly overhead in the same hemisphere as where parallel-plate solar-redshift system 300 is located, the inclination angle of the base support 460 may be less than 90°. While the sun 500 is directly overhead in the opposite hemisphere from where parallel-plate solar-redshift system 300 is located, the inclination angle of the base support 460 may be greater than 90°. Inclination angles greater than 90° may be accomplished, for example, by moving the pivot point 465 up the base support 460 a suitable distance to cause the parallel-plate solar-redshift system 300 to rock back and forth.

The schematics of FIGS. 11A and 11B illustrate that the parallel-plate solar-redshift system 300 according to embodiments herein may have a dual-axis tracking ability with only the level of external movement apparatus that would be required in a single-axis tracking system. In particular, to track the sun over the course of a year, an elevational adjustment mechanism (such as one that moves the base support 460 relative to the support structure 450, for example) may be required to lower the inclination angle from the summer inclination angle $\theta_1$ to the winter inclination angle $\theta_2$ or to raise the inclination angle from the winter inclination angle $\theta_2$ to the summer inclination angle $\theta_1$. Tracking the sun during the course of a single day, on the other hand, may be accomplished with a less substantial apparatus that may be easier to maintain than an apparatus requiring rotation of the entire parallel-plate solar-redshift system 300 to follow the azimuthal location of the sun, for example. In particular, the azimuthal focus adjustment mechanism 410 that moves the at least one focusing device 340 relative to the parallel-plate configuration 301 may be used to efficiently and accurately maintain focus of the incident solar radiation 510 on the sun-facing edges 355 of the waveguides 350 (see FIGS. 6 and 7, for example).

Thus, various embodiments of solar-redshift systems have been described in detail provided, in each of which quantum dots may be used to convert high-energy wavelengths in broad-spectrum incident solar radiation to selected lower-energy wavelengths, so as to improve efficiency for a specific energy-harnessing application, such as photosynthetic or photovoltaic conversion. The solar-redshift systems are configured not only to optimize the wavelength spectrum of the solar radiation, but also to maximize the efficiency at which the solar radiation is made available to the energy-harnessing application. Particular solar-redshift systems described herein may also mitigate or eliminate the need for incorporating equipment-intensive dual-axis tracking mechanisms.

Unless otherwise defined, all technical and scientific terms used herein have the same meaning as commonly understood by one of ordinary skill in the art to which the invention belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

Unless otherwise indicated, all numbers expressing quantities of ingredients, properties such as molecular weight, and so forth as used in the specification and claims are to be understood as being modified in all instances by the term "about." Accordingly, unless otherwise indicated, the numerical properties set forth in the specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. One of ordinary skill in the art will understand that any numerical values inherently contain certain errors attributable to the measurement techniques used to ascertain the values.

As used herein, the terms "horizontal" and "vertical" are relative terms only, are indicative of a general relative orientation only, and do not necessarily indicate perpendicularity. These terms, as well as terms such as "left," "right," "into the plane," and "out of the plane" also may be used for convenience to refer to orientations used in the figures, which orientations are used as a matter of convention only and are not intended as characteristic of the devices shown, except where explicitly noted to the contrary. The embodiments described herein may be used in any desired orientation.

It should be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A redshift system comprising:
    a collecting target comprising a target wavelength;
    a quantum dot vessel comprising quantum dots disposed therein, the quantum dots emitting redshifted light comprising the target wavelength in response to being irradiated by electromagnetic radiation comprising a wavelength different than the target wavelength;
    a waveguide interposed between the collecting target and the quantum dot vessel; and
    a focusing device configured to focus the electromagnetic radiation comprising the wavelength different than the target wavelength on an edge of the waveguide;
    wherein the collecting target, the waveguide, and the quantum dot vessel are arranged in a parallel-plate configuration; and
    wherein the waveguide comprises a frustrating surface configured to scatter the focused electromagnetic radiation within the waveguide toward the quantum dot vessel and permit redshifted light emitted by the quantum dot vessel to pass through the waveguide toward the collecting target.

2. The redshift system of claim 1, wherein the quantum dot vessel comprises a first quantum dot vessel and a second quantum dot vessel, the collecting target is positioned between the first quantum dot vessel and the second quantum dot vessel, and the waveguide comprises a first waveguide interposed between the collecting target and the first quantum dot vessel and a second waveguide interposed between the collecting target and the second quantum dot vessel.

3. The redshift system of claim 1, wherein the quantum dot vessel comprises a sealed cavity defined between a first plate and a second plate.

4. The redshift system of claim 1, wherein the quantum dot vessel comprises a trapping reflector that reflects a portion of the redshifted light emitted by the quantum dots toward the collecting target and transmits infrared light from the electromagnetic radiation in a direction away from the collecting target.

5. The redshift module of claim 4, wherein the trapping reflector is configured to transmit in the direction away from the collecting target at least 50% of infrared light comprising a wavelength of from 700 nm to 1 mm.

6. The redshift system of claim 1, wherein the focusing device comprises a fresnel lens or an array of converging lenses.

7. The redshift system of claim 1, further comprising an azimuthal focus adjustment mechanism that changes a focal distance of the focusing device from the edge of the waveguide.

8. The redshift system of claim 7, wherein the electromagnetic radiation comprises incident solar radiation, the edge of the waveguide comprises a sun-facing edge that is aligned from east to west, and changing the focal distance of the focusing device with the azimuthal focus adjustment mechanism over the course of a day maintains focus of the incident solar radiation on the sun-facing edge of the waveguide.

9. The redshift system of claim 1, further comprising an elevational adjustment mechanism that adjusts an elevational angle of the redshift system over the course of a year.

10. The redshift system of claim 1, wherein the waveguide is configured to trap the focused electromagnetic radiation by total internal reflection, and the frustrating surface of the waveguide comprises scattering features configured to scatter the focused solar radiation within the waveguide toward the quantum dot vessel.

11. The redshift system of claim 1, further comprising an infrared-radiation absorber, wherein the quantum dot vessel is interposed between the waveguide and the infrared-radiation absorber, and the collecting target, the waveguide, the quantum dot vessel, and the infrared-radiation absorber are arranged in the parallel-plate configuration.

12. The redshift system of claim 11, wherein the infrared-radiation absorber comprises a photovoltaic plate comprising a photovoltaic material.

13. The redshift module of claim 1, wherein the collecting target comprises a growth vessel for containing a living photosynthetic organism, and the target wavelength comprises a wavelength of increased photosynthetic response of the living photosynthetic organism.

14. The redshift module of claim 13, wherein the living photosynthetic organism comprises algae.

15. The redshift system of claim 13, wherein the living photosynthetic organism is selected from the group consisting of green algae, cyanobacteria, *Synechocystis* sp., and *Chlorella vulgaris*.

16. The redshift system of claim 1, wherein the collecting target comprises a photovoltaic plate.

17. A redshift system comprising:
a collecting target comprising a target wavelength;
an infrared-radiation absorber;
a waveguide interposed between the collecting target and the infrared-radiation absorber;
a focusing device configured to focus electromagnetic radiation comprising a wavelength different than the target wavelength on an edge of the waveguide; and
a quantum dot vessel interposed between the waveguide and the infrared-radiation absorber and comprising quantum dots disposed therein, the quantum dots emitting redshifted light comprising the target wavelength in response to being irradiated by the electromagnetic radiation comprising the wavelength different than the target wavelength;
wherein the collecting target, the infrared-radiation absorber, the waveguide, and the quantum dot vessel are arranged in a parallel-plate configuration; and
wherein the waveguide comprises a frustrating surface configured to scatter the focused electromagnetic radiation within the waveguide toward the quantum dot vessel and permit redshifted light emitted by the quantum dot vessel to pass through the waveguide toward the collecting target, and the quantum dot vessel comprises a trapping reflector that reflects a portion of the redshifted light emitted by the quantum dots toward the collecting target and transmits infrared light from the electromagnetic radiation toward the infrared-radiation absorber.

18. A redshift module comprising:
a first collecting target and a second collecting target, the first collecting target and the second collecting target comprising a target wavelength;
a quantum dot vessel comprising quantum dots disposed therein, the quantum dots emitting redshifted light comprising the target wavelength in response to being irradiated by electromagnetic radiation comprising a wavelength different than the target wavelength; and
a focusing device configured to focus the electromagnetic radiation through a focusing gap and toward the quantum-dot vessel, the focusing gap defined between a first edge of the first collecting target and a second edge of the second collecting target;
wherein the first collecting target and the second collecting target are each positioned between the focusing device and the quantum-dot vessel, and the focusing device, the quantum-dot vessel, the first collecting target and the second collecting target are arranged such that the electromagnetic radiation focused through the focusing gap strikes the quantum-dot vessel without first striking the first collecting target and the second collecting target.

19. A redshift module comprising:
a collecting target comprising a target wavelength;
a first quantum-dot vessel and a second quantum-dot vessel comprising quantum dots disposed therein, the quantum dots emitting redshifted light comprising the target wavelength in response to being irradiated by electromagnetic radiation comprising a wavelength different than the target wavelength; and
a focusing device configured to focus the electromagnetic radiation through a focusing gap, the focusing gap being defined between the first quantum-dot vessel and the second quantum-dot vessel, the focusing device configured to focus the electromagnetic radiation through the focusing gap and onto a plate reflector, and the plate reflector configured to reflect the electromagnetic radiation toward at least one of the first quantum-dot vessel or the second quantum-dot vessel;
wherein the first quantum-dot vessel and the second quantum-dot vessel are each positioned between the focusing device and the collecting target, and the focusing device, the first quantum-dot vessel, the second quantum-dot vessel, and the collecting target are arranged such that the electromagnetic radiation focused through the focusing gap strikes at least one of the first quantum-dot vessel or the second quantum-dot vessel without first striking the collecting target.

* * * * *